(12) United States Patent
Tessier

(10) Patent No.: US 9,792,465 B2
(45) Date of Patent: Oct. 17, 2017

(54) AUTOMATIC TOUCH IDENTIFICATION SYSTEM AND METHOD THEREOF

(71) Applicant: KONINKLIJKE PHILIPS N.V., Eindhoven (NL)

(72) Inventor: Paul Tessier, Lynnfield, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/278,662

(22) Filed: May 15, 2014

(65) Prior Publication Data

US 2014/0246491 A1 Sep. 4, 2014

Related U.S. Application Data

(63) Continuation of application No. 14/106,058, filed on Dec. 13, 2013, now abandoned, which is a (Continued)

(51) Int. Cl.
| | |
|---|---|
| *G06K 5/00* | (2006.01) |
| *G06K 7/01* | (2006.01) |
| *G06K 7/08* | (2006.01) |
| *G06K 7/10* | (2006.01) |
| *G06K 19/07* | (2006.01) |

(Continued)

(52) U.S. Cl.
CPC ............. *G06K 7/01* (2013.01); *G06K 7/0013* (2013.01); *G06K 7/08* (2013.01); *G06K 7/10326* (2013.01); *G06K 19/07* (2013.01); *G06K 19/07743* (2013.01); *G06F 19/327* (2013.01); *G08B 21/0453* (2013.01); *G08B 21/0461* (2013.01); *G08B 21/245* (2013.01)

(58) Field of Classification Search
USPC .......................... 235/380, 487, 375, 492, 451
See application file for complete search history.

(56) References Cited

U.S. PATENT DOCUMENTS

| | | | |
|---|---|---|---|
| 5,811,897 | A | 9/1998 | Spaude et al. |
| 6,002,427 | A | 12/1999 | Kipust |

(Continued)

OTHER PUBLICATIONS

Mikki, Said M. et al., "Theory and Applications of Infinitesimal Dipole Models for Computational Electromagnetics," IEEE Transactions on Antennas and Propagation, vol. 55(5):1325-1337 (2007).

(Continued)

*Primary Examiner* — Edwyn Labaze
(74) *Attorney, Agent, or Firm* — Larry Liberchuk

(57) ABSTRACT

An automatic identification system for communicating identifying information by coupling signals through the human body is provided. The system includes a battery powered identification device that transmits an identifying signal via a modulated carrier. The identification device is coupled to the body of the user via a coupling plate. The signal from the identification device is received by a reading device that is also coupled to the body of the user via a coupling plate. The reading device may display and/or enunciates the identifying information to the user. The coupling technique, carrier frequency, and construction of the devices are such that the identification information is not inadvertently radiated or coupled to unintentional users or receivers.

19 Claims, 29 Drawing Sheets

Related U.S. Application Data continuation of application No. 13/661,415, filed on Oct. 26, 2012, now Pat. No. 8,668,145, which is a continuation-in-part of application No. 12/764,699, filed on Apr. 21, 2010, now Pat. No. 8,297,499.

(60) Provisional application No. 61/171,206, filed on Apr. 21, 2009.

(51) Int. Cl.
   *G06K 19/077* (2006.01)
   *G06K 7/00* (2006.01)
   *G06F 19/00* (2011.01)
   *G08B 21/04* (2006.01)
   *G08B 21/24* (2006.01)

(56) References Cited

U.S. PATENT DOCUMENTS

| | | | |
|---|---|---|---|
| 6,104,913 A | 8/2000 | McAllister | |
| 6,223,018 B1 | 4/2001 | Fukumoto et al. | |
| 6,337,667 B1* | 1/2002 | Ayala | H01Q 1/243 343/702 |
| 6,542,717 B1 | 4/2003 | Zimmerman et al. | |
| 6,570,610 B1 | 5/2003 | Kipust | |
| 6,754,472 B1 | 6/2004 | Williams et al. | |
| 6,771,161 B1 | 8/2004 | Doi et al. | |
| 6,823,171 B1 | 11/2004 | Kaario | |
| 6,864,780 B2 | 3/2005 | Doi et al. | |
| 7,206,423 B1 | 4/2007 | Feng et al. | |
| 7,262,701 B1* | 8/2007 | Nguyen | H01Q 1/2225 340/572.4 |
| 7,267,262 B1 | 9/2007 | Brown | |
| 7,352,996 B2 | 4/2008 | Kumar | |
| 7,583,930 B2 | 9/2009 | Minotani et al. | |
| 7,832,646 B1 | 11/2010 | Leason | |
| 8,881,373 B1* | 11/2014 | Koepp | 29/592.1 |
| 2002/0117543 A1* | 8/2002 | Kocznar et al. | 235/380 |
| 2003/0189096 A1 | 10/2003 | Markkanen et al. | |
| 2004/0073127 A1* | 4/2004 | Istvan | A61B 5/0006 600/513 |
| 2004/0205350 A1* | 10/2004 | Waterhouse | G06Q 10/08 713/182 |
| 2006/0061515 A1* | 3/2006 | Posluszny | H01Q 1/243 343/803 |
| 2008/0246613 A1 | 10/2008 | Linstrom et al. | |
| 2008/0308641 A1 | 12/2008 | Finn | |
| 2009/0001930 A1* | 1/2009 | Pohjonen | H01Q 1/2225 320/108 |
| 2010/0026461 A1* | 2/2010 | Merchan | G06K 19/0723 340/10.1 |
| 2010/0030167 A1* | 2/2010 | Thirstrup | A61F 5/445 604/318 |
| 2010/0093428 A1* | 4/2010 | Mattice | G07F 17/3251 463/25 |
| 2011/0024512 A1* | 2/2011 | Satake | H01Q 1/2208 235/492 |
| 2011/0118030 A1* | 5/2011 | Walley et al. | 463/37 |
| 2011/0227856 A1* | 9/2011 | Corroy | H04B 13/005 345/173 |
| 2012/0139710 A1* | 6/2012 | Burr | 340/10.1 |
| 2014/0348270 A1* | 11/2014 | Babu et al. | 375/317 |

OTHER PUBLICATIONS

Webster, J. (ed.), "Dipole Antennas," Wiley Encyclopedia of Electric and Electronics Engineering, John Wiley & Sons, Inc., pp. 575-581 (1999).

* cited by examiner

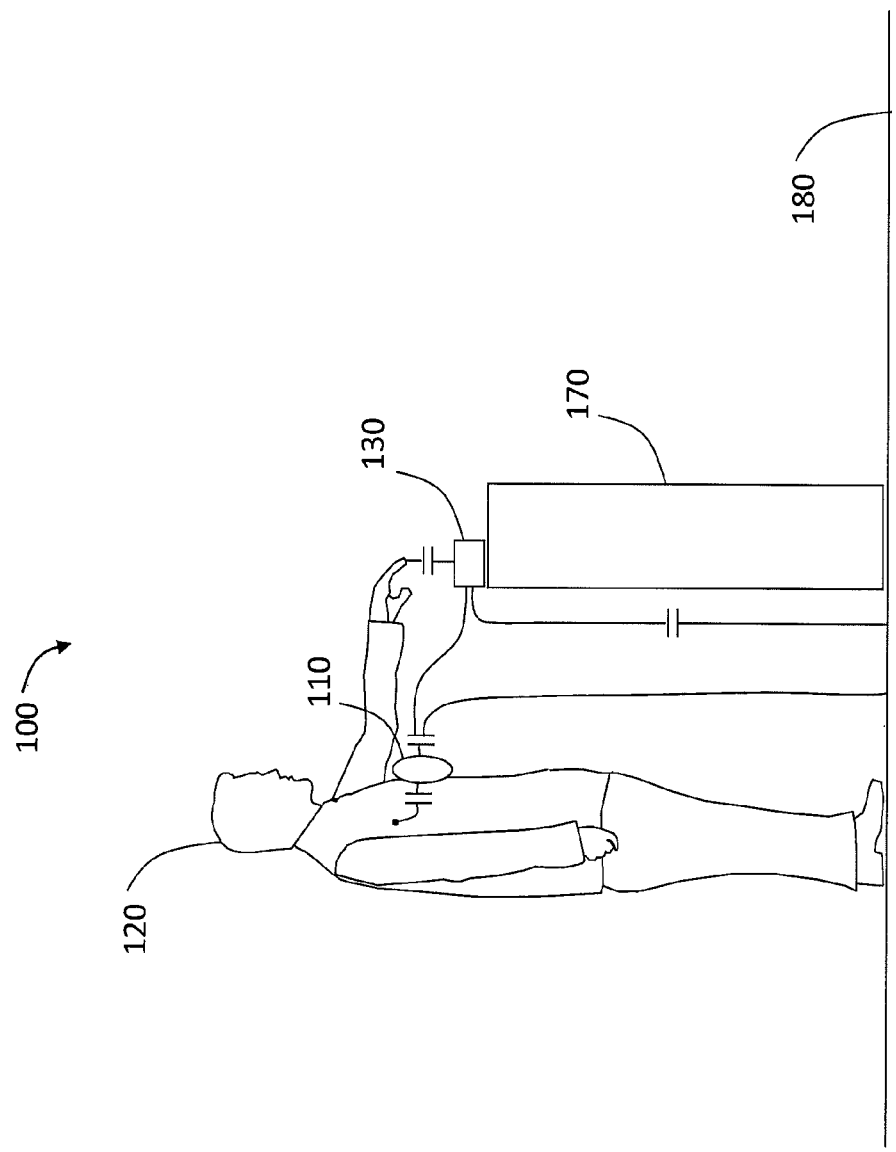

AUTOMATIC TOUCH IDENTIFICATION SYSTEM AND METHOD THEREOF

RELATED APPLICATIONS

The present application is a continuation of U.S. application Ser. No. 14/106,058 entitled "Automatic Touch Identification System and Method Thereof", filed on Dec. 13, 2013, which is a continuation of U.S. application Ser. No. 13/661,415, filed on Oct. 26, 2012, which is a continuation in part of U.S. application Ser. No. 12/764,699, filed on Apr. 21, 2010, which claims priority to U.S. Provisional Patent Application Ser. No. 61/171,206, filed Apr. 21, 2009, the contents of which are herein incorporated by reference.

BACKGROUND OF THE INVENTION

There is a need to identify objects and people ("objects") automatically. Automatically determining identity eliminates human error, makes the identification process faster, and allows direct interfacing with computing systems and related applications. The most common types of automatic identification in use today include barcodes, RFID labels, and magnetic cards. Automatic identification is used for applications such as identifying items in inventory or for checkout, providing entry into secured areas, logging into a computer system, facilitating rental car returns, positively identifying patients in hospitals, ensuring the proper medication is being delivered, and numerous other applications. Unfortunately the systems used today have many drawbacks and inadequacies. Conventional systems typically require the user to hold a reading device (such as a barcode scanner), or to hold an identification device (such as an ID card) thus tying up the user's hands. In addition, these systems only work when a barcode, RFID tag, or magnetic card is properly scanned. Most scanners only work a very short distance, require that the barcode, RFID tag, or magnetic card be correctly oriented to the reader, and frequently do not read correctly on the first scan, making them inadequate for many applications. Real time location systems ("RTLS") can also provide automatic identity, but are large and complex systems that are expensive and difficult to install and maintain. In addition most location systems do not have the spatial or temporal accuracy required for most automatic identification applications.

The drawbacks and inadequacies of current systems create significant compromises in many applications. For example ID cards containing a barcode, magnetic strip, or RFID chip are commonly used to unlock a door for access to restricted areas. People desiring to enter the area must scan the card at a reader near the door. The person must retrieve the ID card from a pocket, wallet, or purse, and orient it correctly to the reader. If the card is not oriented correctly or not read properly by the reader, the person must repeat the operation. This process can be time consuming and frustrating to the user.

Similar ID card systems are used to authorize access to computer systems. Frequently these systems are used together with a password to provide positive user identification and access to the system. These systems have many of the same problems as entry access systems. People desiring to access the computer must scan the card at a reader. The person must retrieve the card from a pocket, wallet, or purse, and orient it correctly to the reader. If the card is not oriented correctly or not read properly by the reader, the person must repeat the operation. This process can be time consuming and frustrating to the user. Frequently the user will set the ID card down on the work surface next to the computer and forget to pick it up when they are finished with their task, which can lead to a lost card and/or a security risk. Another problem with these systems is that people frequently forget to logoff when they have completed their tasks and simply walk away from the computer. When this happens, an unauthorized person can then walk up to the computer and have unauthorized access. In an attempt to prevent this problem from occurring some computer systems automatically log a user off if there is isn't keyboard activity for some period of time. If the timeout period is too short then users get logged off inadvertently. A user may turn to talk briefly to a colleague and turn back to the computer only to find that they have been logged off. If the timeout period is too long and the user forgets to logoff then there is a period of venerability for unauthorized access.

The need for an improved computer authorization system is particularly evident in hospitals where mobile care providers access many different computer systems on a frequent basis and are faced with strict HIPPA rules for patient confidentiality. Hospitals can also benefit from other applications of automatic identification systems. Another example is positive patient identification. Clinical personnel need to positively identify patients prior to administering medication or performing procedures. Hospitals have tried to utilize barcodes and RFID tags located on patient's wrist bands for this purpose. This requires that the clinician use a reading device which means the clinician must be located next to the reading device, search for a portable device, or ensure that he has a portable reader on him at all times. This creates issues in spending time searching for a reader, or the hassle of carrying a reader. There is also the issue of limited battery life in portable readers, where even if the clinician has a device available it might not be usable due to a low battery. In addition it can be difficult to scan the barcode or RFID tag since it is located on the patient's wrist and can be in a variety of positions making it difficult to properly align the reader or even get the reader near the ID band.

A touch identification system could also enable new applications such as automatically determining whether personnel are complying with hand washing requirements. In many jobs, such as food-workers and hospital-workers, there are requirements for hand-washing to ensure public safety. Unfortunately these policies are frequently not followed. To ensure compliance it would be desirable to have a system that automatically determined that an employee activated the soap dispenser and logged the event.

Another application of a touch identification system is to monitor activities of daily living of the elderly. Many elderly desire to live independently rather than live with a relative or enter an assisted living facility. Unfortunately it can be risky for the elderly to live independently. Issues like chronic illness, medication errors, forgetfulness, depression, not eating well, and falling greatly complicate the situation. To assist the elderly in their desire to live independently, it would be desirable to have a system that automatically monitored activities of daily living that could detect issues in time for corrective action to be taken.

Technologies and products have been developed to provide communication of information through or on the body of a user, but these technologies and products have not been broadly adopted due to their significant drawbacks and inadequacies. Many of these technologies and products require very specific placement of devices on the body of the user and/or require multiple contact points—some including ground connections—making them impractical to use. Most of these technologies and products do not address the issue of communication signals inadvertently radiating or coupling from the devices or the user, which could result in signals being wrongly communicated creating security issues with the system. There is also the issue of unreliable performance due to users having different body characteristics such as body mass and skin impedance and environmental issues causing variable stray coupling of the user to objects in the environment.

SUMMARY OF THE INVENTION

Accordingly, it would be beneficial to have an automatic touch identification system that identified objects (e.g. people and things) by the user having a device on his/her person and simply touching, or coming in very close proximity to, a device located on another object, that was inexpensive, simple to use, secure, and worked well with different user characteristics and body types.

It would also be desirable to have an entry control system that automatically identified a person if they had an ID device on their person and simply touched a spot on a reader next to the door or the door handle itself.

A computer authorization system may automatically identify a person with an ID device on their person when the person touched the keyboard area of the computer. The system may also be used as a log-in log-off system in connection with computers. For example, the system may keep the user logged-on as long as their ID matched the ID read at log-on, but would lock out any attempt of someone without an ID (keyboard activity without a detected ID) or a non-matching ID (keyboard activity with a different ID detected) from using the computer under the initial user's log-on and would automatically log-off the original user.

The identification system may also used by clinicians to access information associated with a patient. For example, the identification system may allow the clinician to touch the patient's wrist or bracelet located on the patient's wrist with his finger and have the ID read automatically.

A hand washing monitoring system may automatically identify a person with an identification device or reading device on their person when the person entered an unsanitary area (e.g. bathroom) and when the person used a soap dispenser and/or faucet. Objects in those areas would have the complementary identification device or reading device allowing information to be communicated when the person touch the objects. The system could provide a prompt to the person and/or notify a supervisor if the person failed to wash his hands prior to returning to work.

The identification system may also be used for activity monitoring for an elderly or infirmed person. Identification devices located on, or built into, objects in the person's home could communicate the objects ID to a reading device worn by the user. Knowing that the person touched an object of a specific ID could allow the system to determine the person's activity. For example, an ID associated with a toilet handle could indicate that the person flushed the toilet.

In accordance with one embodiment, a system is provided for communicating identifying information by coupling signals through the human body. The system includes a battery powered identification device that transmits an identifying signal via a modulated carrier and is coupled to the body of the user with a coupling plate. The signal from the identification device is received by a reading device that is also coupled to the body of the user with a coupling plate. The reading device displays and/or enunciates the identifying information to the user. The coupling technique, carrier frequency, and construction of the devices are such that the identification information is not inadvertently radiated or coupled to unintentional users or receivers.

According to an embodiment, an identification system for transmitting or receiving information via a user comprises an identification device and a reading device. The identification device includes a first coupling module configured to couple the identification device to the user by a capacitive type connection or a galvanic type connection. The reading device includes a second coupling module configured to couple the reading device to the user by a capacitive type connection or a galvanic type connection. The identification device transmits identifying information via the user. The reading device receives the identifying information from the identification device via the user. The first coupling module of the identification device transmits the identifying information to the reading device via the user over a carrier frequency having a frequency less than or equal to about 3 MHz.

In accordance with one embodiment, a method of verifying identifying information from an identification device comprises coupling an identification device to a user via one or more of a capacitive coupling and a galvanic connection using a first coupling module. The method further includes coupling a reading device to the user via one or more of a capacitive coupling and a galvanic connection using a second coupling module. Identifying information is transmitted by the first coupling module from the identification device to the reading device via the user over a carrier frequency having a frequency less than or equal to about 3 MHz. The method also includes receiving, at the reading device, the identifying information transmitted by the identification device via the user.

According to various embodiments, the method may also include establishing a network connection between the reading device and a computing device. The reading device or the computing device may derive information from the identifying information received from the identification device. The method may further include sending, by the reading device, the identifying information or the information derived from the identifying information by the reading device to the computing device over the network connection.

According to another embodiment, a method for using an automatic identification system to control a computer sign-on/sign-off system includes coupling an identification device to a user via one or more of a capacitive coupling and a galvanic connection using a coupling module and coupling a reading device to a computing device. The method further includes transmitting identifying information from the identification device to the reading device via the user when the user establishes one or more of a capacitive coupling and a galvanic connection with the reading device. The method also includes transmitting, by the reading device, the identifying information received from the identification device to the computing device. A logon screen is displayed to the user if the identifying information received from reading device contains valid identifying information. The user is logged on. The method further includes monitoring keyboard activity using the computing device and disabling a display device of the computing device if the keyboard is inactive for a pre-determined amount of time. Keyboard activity is detected using the computing device. The method also includes checking the identifying information sent by the reading device. The method further includes enabling the display device of the computing device if the identifying information remains unchanged or logging off the user if the identifying information received from the reading device has changed.

According to another embodiment, a method for using an automatic identification system to monitor hand washing includes coupling an identification device or reading device to a user via one or more of a capacitive coupling and a galvanic connection using a coupling module and coupling a reading device to a computing device. The method further includes transmitting identifying information from the identification device to the reading device via the user when the user establishes one or more of a capacitive coupling and a galvanic connection with a complementary reading device or identification device. The method also includes transmitting, by the reading device, the identifying information received from the identification device to the computing device. The method further includes monitoring the user's activity to determine whether the user is coupled or connected with an identification device or reading device associated with an unclean object. The method also includes checking that the user washed his hands following contact with the unclean object by watching for user coupling or connection with an identification device or reading device associated with hand washing such as a soap dispenser.

According to another embodiment, a method for using an automatic identification system to monitor activities of daily living includes coupling an identification device or reading device to a user via one or more of a capacitive coupling and a galvanic connection using a coupling module and coupling a reading device to a computing device. The method further includes transmitting identifying information from the identification device to the reading device via the user when the user establishes one or more of a capacitive coupling and a galvanic connection with a complementary reading device or identification device. The method also includes transmitting, by the reading device, the identifying information received from the identification device to the computing device. The method further includes monitoring the user's activity, logging that activity in the computing device, and providing alerts and reports based on the user's activity.

Suitable methods can be employed to implement the foregoing system and accordant functionality.

DESCRIPTION OF DRAWINGS

The invention will be apparent from the description herein and the accompanying drawings, in which like reference characters refer to the same parts throughout the different views.

FIG. 2B is an illustrative depiction of another embodiment of an automatic touch identification system of the present invention showing the coupling and signal paths for an identifying signal;

DETAILED DESCRIPTION

The illustrative embodiment of the present invention provides a system and method of identifying objects by the user simply touching, or coming in very close proximity to, a device located on another object while preventing the identification information from being inadvertently radiated or coupled to unintentional receivers. As used herein objects can be items, things, people, or animals of any type that can be used with the identification device or reading device of the present invention.

Figure 1A:
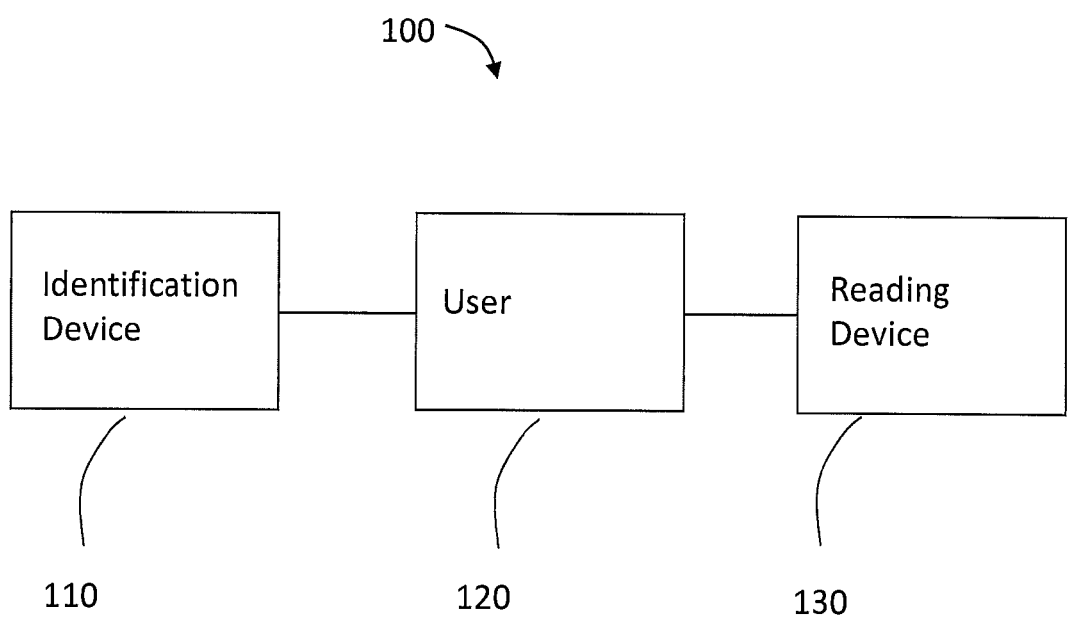
FIG. 1A is a schematic block diagram of an automatic touch identification system according to the teachings of the present invention.

FIG. 1A depicts one embodiment of an automatic touch identification system 100 suitable for practicing an illustrative embodiment of the present invention. According to this embodiment, the automatic touch identification system 100 includes an identification device 110 and a reading device 130 that are coupled to the user 120. According to various embodiments of the present invention, the identification device 110 may send identifying information such as an identifying signal to the reading device 130. The identification information may be sent, conducted or otherwise transmitted by the identification device 110 to the reading device 130 via the user 120.

Figure 1B:
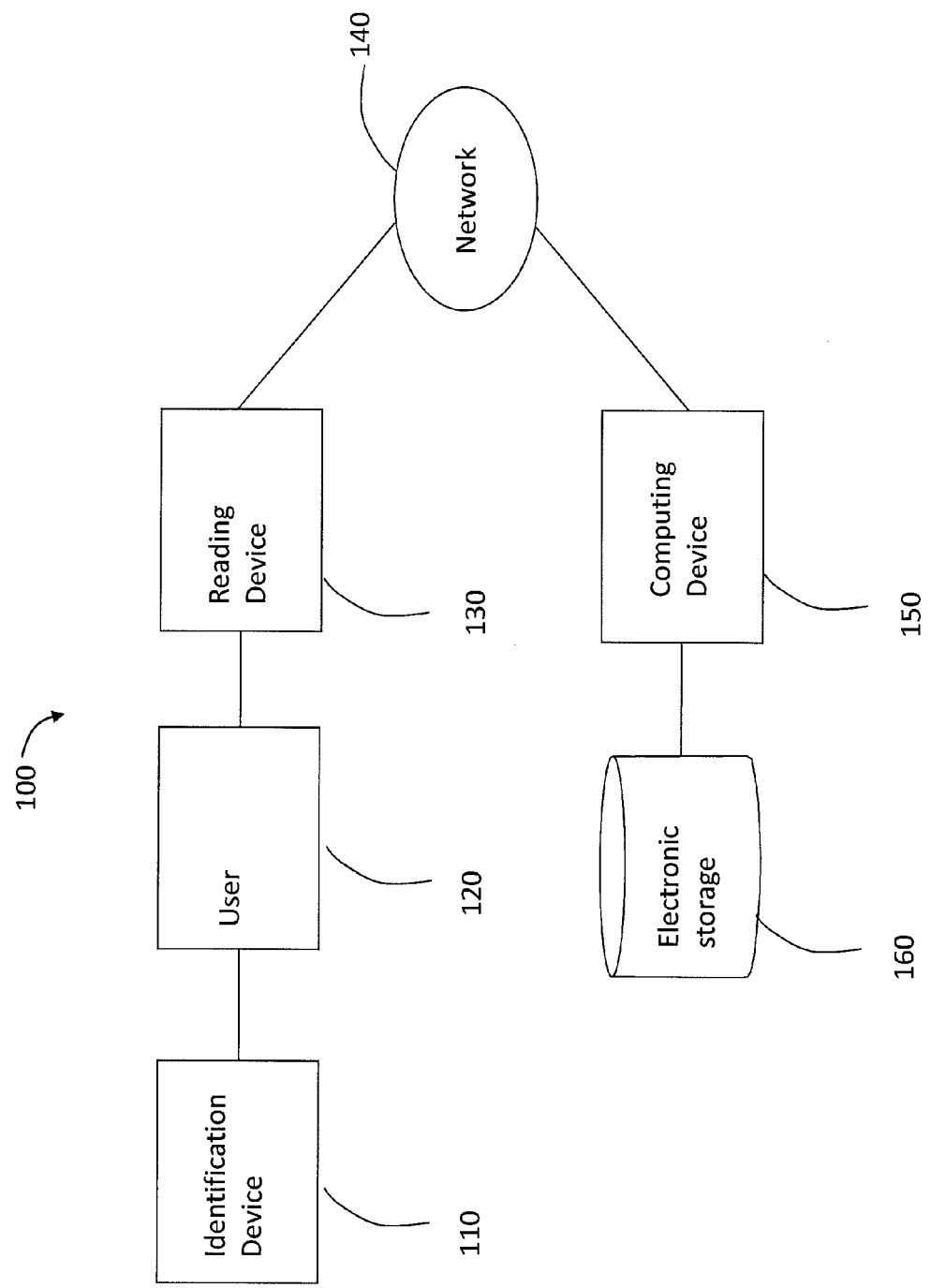
FIG. 1B is a schematic block diagram of another embodiment of an automatic touch identification system according to the teachings of the present invention.

Another embodiment of an automatic touch identification system 100 suitable for practicing an illustrative embodiment of the present invention is illustrated in FIG. 1B. In this embodiment, the exemplary automatic touch identification system 100 may include the identification device 110, the reading device 130 that are coupled to the user 120. The exemplary automatic touch identification system 100 may also include a computing device 150 and an electronic storage 160 that communicate with the reading device 130 over a network connection 140. According to the embodiment illustrated in FIG. 1B, the reading device 130 may send or transmit identifying information of the reading device and the identifying information received from identification device 110 and through the network 140 to the computing device 150.

As used herein the term network is intended to include any wired or wireless communication means including but not limited to wireless local area networks (e.g. 802.11, 802.15, infrared, Bluetooth), wireless wide area networks, paging systems, cellular telephony, medical telemetry, a satellite network, USB, Firewire, RS232, RS485, CAN, I²C, a parallel bus or some other type of network or combination thereof. As used herein the term computing device is intended to include any computational device either hardware or software or a combination of both such as a personal computer, server, personal digital assistant (PDA), cell phone or some other type of computational device capable of receiving the identifying information.

The computing device 150 may use the identifying information from identification device 110 and reading device 130 for purposes such as unlocking a door, resetting an alarm, initiating or maintaining a computer logon, or other purpose. Computing device 150 may also place the identifying information and related information into electronic storage 160 which may be accessed by other systems. As used herein, the term electronic storage is intended to include any data storage medium such as a database, memory, registers, RAM, DRAM, EPROM, EEPROM, flash, a disk drive, or other storage means.

Figure 2A:
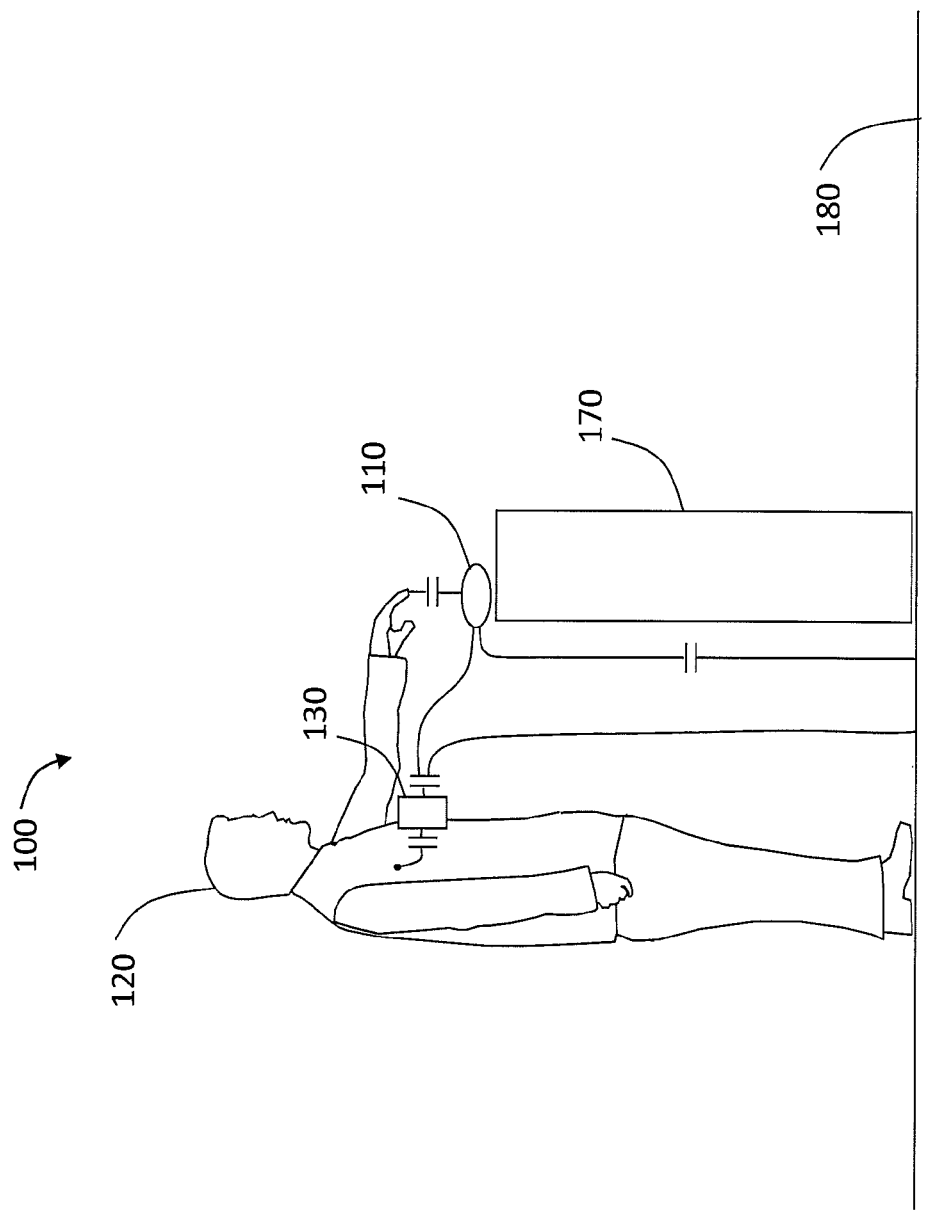
FIG. 2A is an illustrative depiction of an automatic touch identification system of the present invention showing the coupling and signal paths for an identifying signal.

In both of the embodiments illustrated in FIGS. 1A and 1B the reading device 130 may be worn or carried by the user 120 and the identification device 110 may be worn, carried or otherwise attached to another object 170, or identification device 110 may be worn or carried by the user 120 and the reading device 130 may be worn, carried or otherwise attached to another object 170. FIG. 2A illustrates an embodiment of an automatic touch identification system 100 where the reading device 130 is worn by the user 120 and the identification device 110 is attached to another object 170. In this embodiment reading device 130 is coupled to the body of user 120. When user 120 touches or comes in very close proximity to identification device 110 the identification device 110 becomes coupled to the user 120.

Reading device 130 and identification device 110 may be coupled directly together or through other objects such as the floor 180 which completes the circuit. Another embodiment is illustrated in FIG. 2B where the identification device 110 is worn by the user 120 and the reading device 130 is attached to another object 170. In this embodiment identification device 110 is coupled to the body of user 120. When user 120 touches or comes in very close proximity to reading device 130, the reading device 130 becomes coupled to the user 120. Reading device 130 and identification device 110 may be coupled directly together or through other objects such as the floor 180 which completes the circuit. As used herein the term "coupled" is intended to include capacitive coupling, a galvanic connection, a combination of capacitive coupling and a galvanic connection, or other coupling means.

Figure 3A:
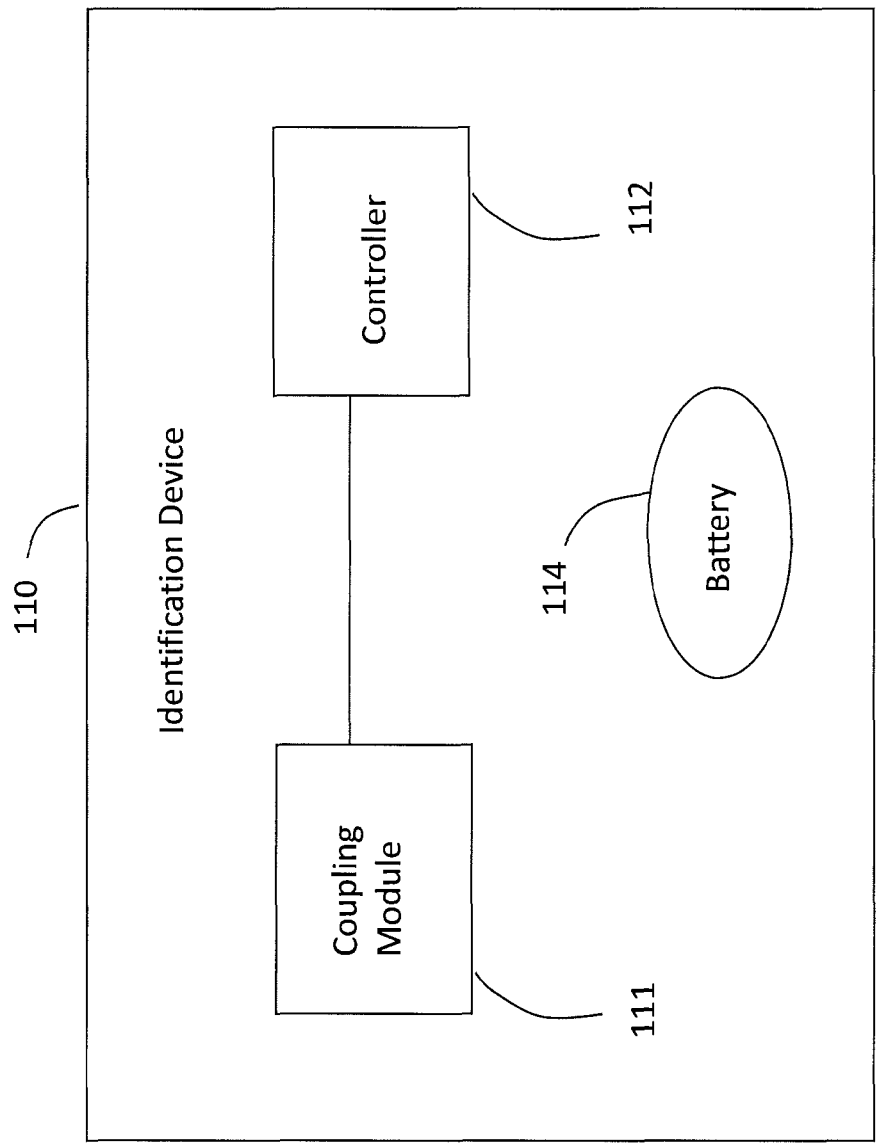
FIG. 3A is a schematic block diagram of an identification device according to the teachings of the present invention.

An example of an identification device 110 according to an embodiment of the invention is illustrated in FIG. 3A. In this embodiment identification device 110 contains a coupling module 111 capable of coupling a signal to a user 120. The coupling module 111 may include a coupling plate that is discussed in further detail below in connection with FIGS. 10A and 10B. The coupling module couples the identifying signal representing the identifying information to the user and generates the carrier frequency to relay the signal to the reading device. According to various embodiments of the present invention, the coupling module may also include a small coil or a trace on a PC board as means for coupling the identification device 110 to the user 120. The coupling module 111 may use capacitive coupling, a galvanic connection, a combination of capacitive coupling and a galvanic connection, or other means to couple a signal to the user 120. Coupling module 111 also generates a carrier frequency and performs modulation of the identifying signal. According to this embodiment, a controller 112 determines the transmission period, duration and content of the identifying signal. In this embodiment the identifying signal is sent on a periodic basis so as to be available when the user touches or comes in close proximity to the identification device 110. The controller 112 may be provided in the form of hardware or software or a combination of both such as a microcontroller or microprocessor running firmware, a field programmable gate array (FPGA) or other such means. The identifying information sent by identification device 110 may include a name, number, classification, type, or other identifier either unique or not unique. Identification device 110 is powered by battery 114.

Figure 3B:
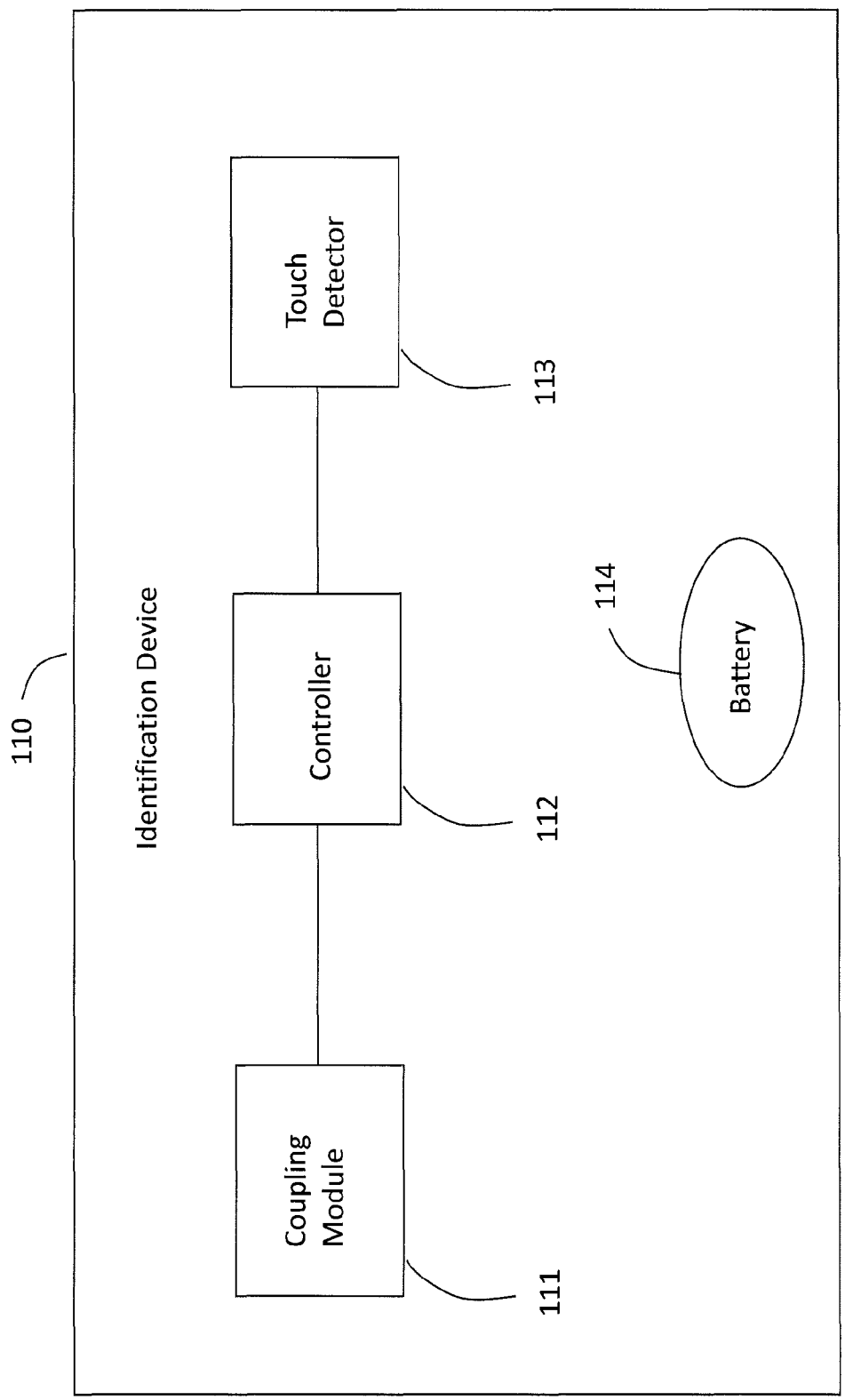
FIG. 3B is a schematic block diagram of another embodiment of an identification device with a touch detector according to the teachings of the present invention.

FIG. 3B illustrates an alternate embodiment of the identification device 110 of the automatic touch identification system 100. In this embodiment identification device 110 contains a coupling module 111 capable of coupling a signal to a user 120. The coupling module 111 may use capacitive coupling, a galvanic connection, a combination of both capacitive coupling and a galvanic connection, or other means to couple a signal to the user. Coupling module 111 also generates a carrier frequency and performs modulation of the identifying signal. According to this embodiment, a controller 112 monitors a touch detector 113 to determine if the user 120 has touched or is in close proximity to identification device 110. Touch detector 113 can be a capacitive sensor or a button contained in identification device 110 or other means to detect that a user is touching identification device 110. When controller 112 determines that a user 120 has touched or is in close proximity to identification device 110 through touch detector 113 it sends an identifying signal. The controller 112 may be provided in the form of hardware or software or a combination of both such as a microcontroller or microprocessor running firmware, a field programmable gate array (FPGA) or other such means. The identifying information sent by identification device 110 may be a name, number, classification, type or other identifier either unique or non-unique. Identification device 110 is powered by battery 114.

Figure 3C:
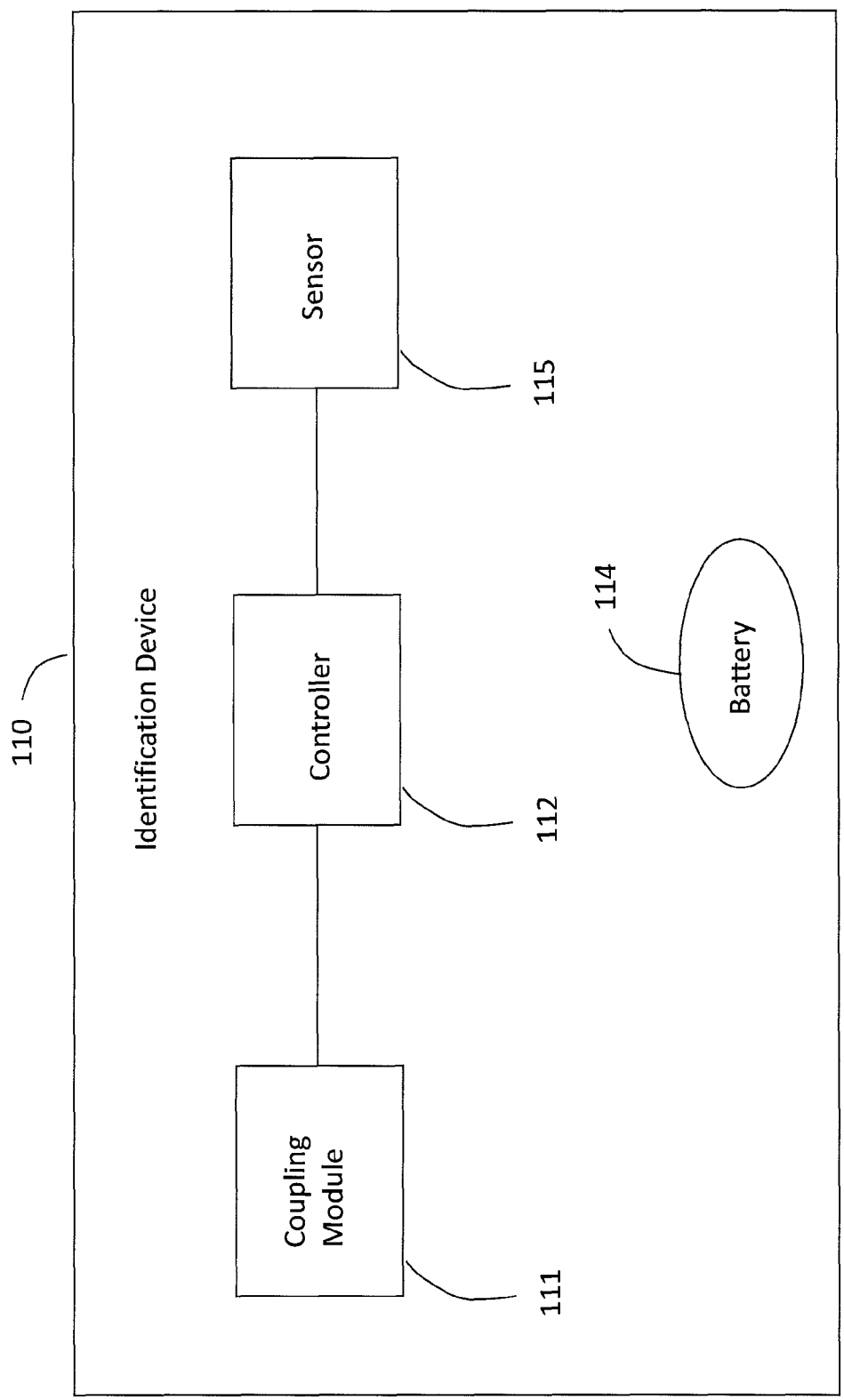
FIG. 3C is a schematic block diagram of another embodiment of an identification device with a sensor according to the teachings of the present invention.

Still yet another embodiment of the identification device 110 of the touch identification system 100 of the present invention is illustrated in FIG. 3C. In this embodiment identification device 110 contains a coupling module 111 capable of coupling a signal to a user 120. The coupling module 111 may use capacitive coupling, a galvanic connection, a combination of both capacitive coupling and a galvanic connection, or other means to couple a signal to the user. Coupling module 111 also generates a carrier frequency and performs modulation of the identifying signal. According to this embodiment, a controller 112 receives data from sensor 115. Sensor 115 may monitor characteristics of the user 120 such as motion, temperature, or blood pressure, or may monitor characteristics of the user's environment such as temperature or humidity, or other characters of the user, the environment, or other objects. When user 120 touches or is in close proximity to identification device 110, identifying information is sent by controller 112. The controller 112 may be provided in the form of hardware or software or a combination of both such as a microcontroller or microprocessor running firmware, a field programmable gate array (FPGA) or other such means. The identifying information sent by identification device 110 may include; sensor data, a name, number, classification, type or other identifier either unique or non-unique. Identification device 110 is powered by battery 114.

Figure 4A:
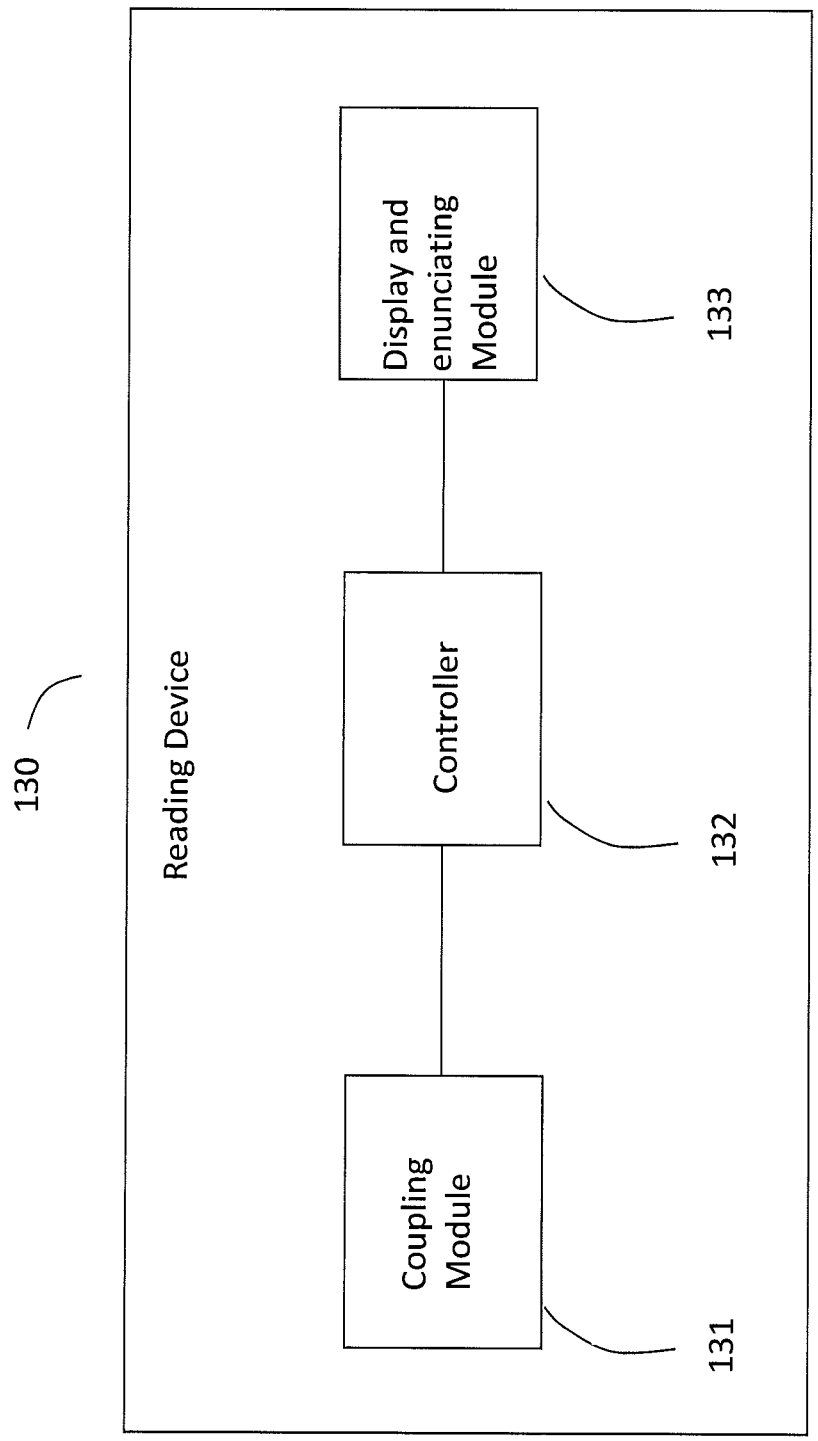
FIG. 4A is a schematic block diagram of a reading device according to the teachings of the present invention.

An example of a reading device 130 according to an embodiment of the invention is illustrated in FIG. 4A. In this embodiment reading device 130 contains a coupling module 131 capable of coupling to a user 120 to receive a signal. The coupling module 131 may use capacitive coupling, a galvanic connection, a combination of both capacitive coupling and a galvanic connection, or other means to couple to a user 120. Coupling module 131 also performs demodulation and/or other conditioning of the received signal. According to this embodiment, a controller 132 receives the identifying signal from coupling module 131 and sends the information to display and enunciating module 133. In this embodiment display and enunciating module 133 displays the information on a visual display and/or enunciates the information through a speaker or headphones. Controller 132 may be provided in the form of hardware or software or a combination of both such as a microcontroller or microprocessor running firmware, a field programmable gate array (FPGA) or other such means. The information displayed or enunciated on display and enunciating module 133 may be the identifying information received by coupling module 131 or may be information derived from, or related to, that identifying information. Derived or related information includes but is not limited to unencrypted information, a name referenced by an identifying number, or other derived information.

Figure 4B:
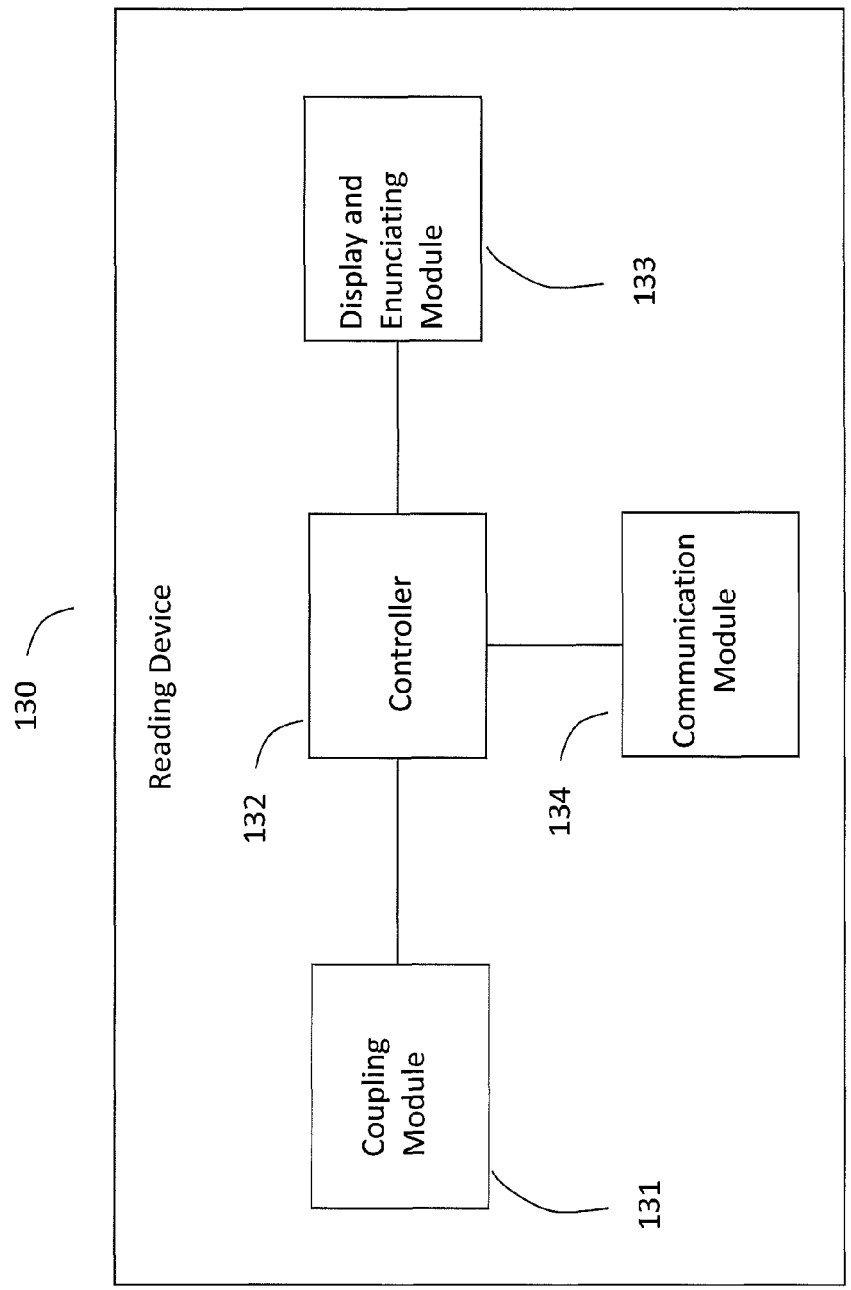
FIG. 4B is a schematic block diagram of another embodiment of a reading device according to the teachings of the present invention.

FIG. 4B illustrates an alternate embodiment of a reading device 130 according to the teachings of the present invention. In this embodiment reading device 130 contains a coupling module 131 capable of coupling to a user 120 to receive a signal. The coupling module 131 may use capacitive coupling, a galvanic connection, a combination of both capacitive coupling and a galvanic connection, or other means to couple to a user 120. Coupling module 131 also performs demodulation and/or other conditioning of the received signal. According to this embodiment, a controller 132 receives the identifying signal from coupling module 131 and sends that information and its own identifying information to communication module 134. Communication module 134 interfaces to network 140 which may be any wired or wireless communication means or a combination of both. The identifying information sourced by reading device 130 may be a name, number, classification, type or other identifier either unique or not unique. According to this embodiment, controller 132 may also send information to display and enunciating module 133.

In this embodiment display and enunciating module 133 displays the information on a visual display and/or enunciates the information through a speaker or headphones. Controller 132 may be provided in the form of hardware or software or a combination of both such as a microcontroller or microprocessor running firmware, a field programmable gate array (FPGA) or other such means. The information displayed or enunciated on display and enunciating module 133 may be the identifying information received by coupling module 131 or may be information derived from or related to that identifying information. Derived information includes but is not limited to unencrypted information, a name referenced by an identifying number, or other derived or related information.

Figure 5A:
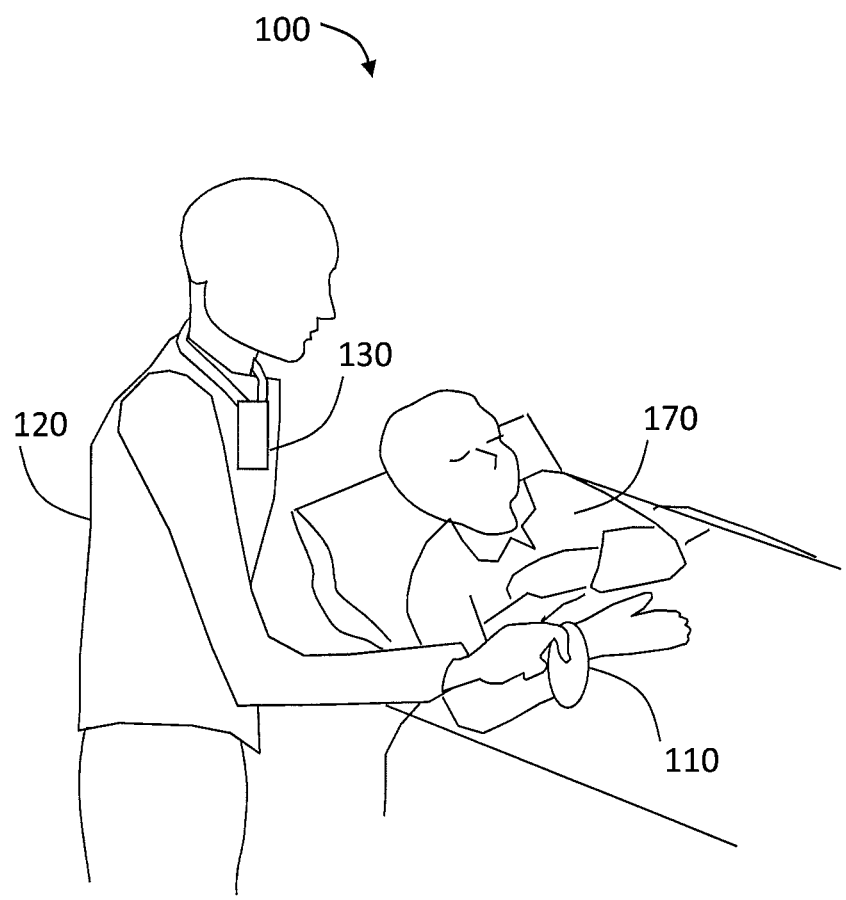
FIG. 5A is an illustrative depiction of the automatic touch identification system of the present invention applied to identifying a patient in a clinical setting.

FIG. 5A depicts one embodiment of an automatic touch identification system 100 suitable for practicing an illustrative embodiment of the present invention applied to identifying a patient in a clinical setting. In this embodiment an identification device 110 is worn on a wristband by a patient (i.e. object 170) which contains identifying information for the patient (i.e. object 170). A clinician (i.e. user 120) is wearing a reading device 130 which is coupled to the clinician (i.e. user 120). According to this embodiment when the clinician (i.e. user 120) touches identifying device 110 the device is also coupled to the clinician (i.e. user 120) and identifying information is conducted or transmitted by or through the clinician (i.e. user 120) to reading device 130. The identifying information may include data about patient (i.e. object 170) obtained from a sensor 115 in identification device 110. Reading device 130 displays and/or enunciates the identifying information to the clinician (i.e. user 120).

Figure 5B:
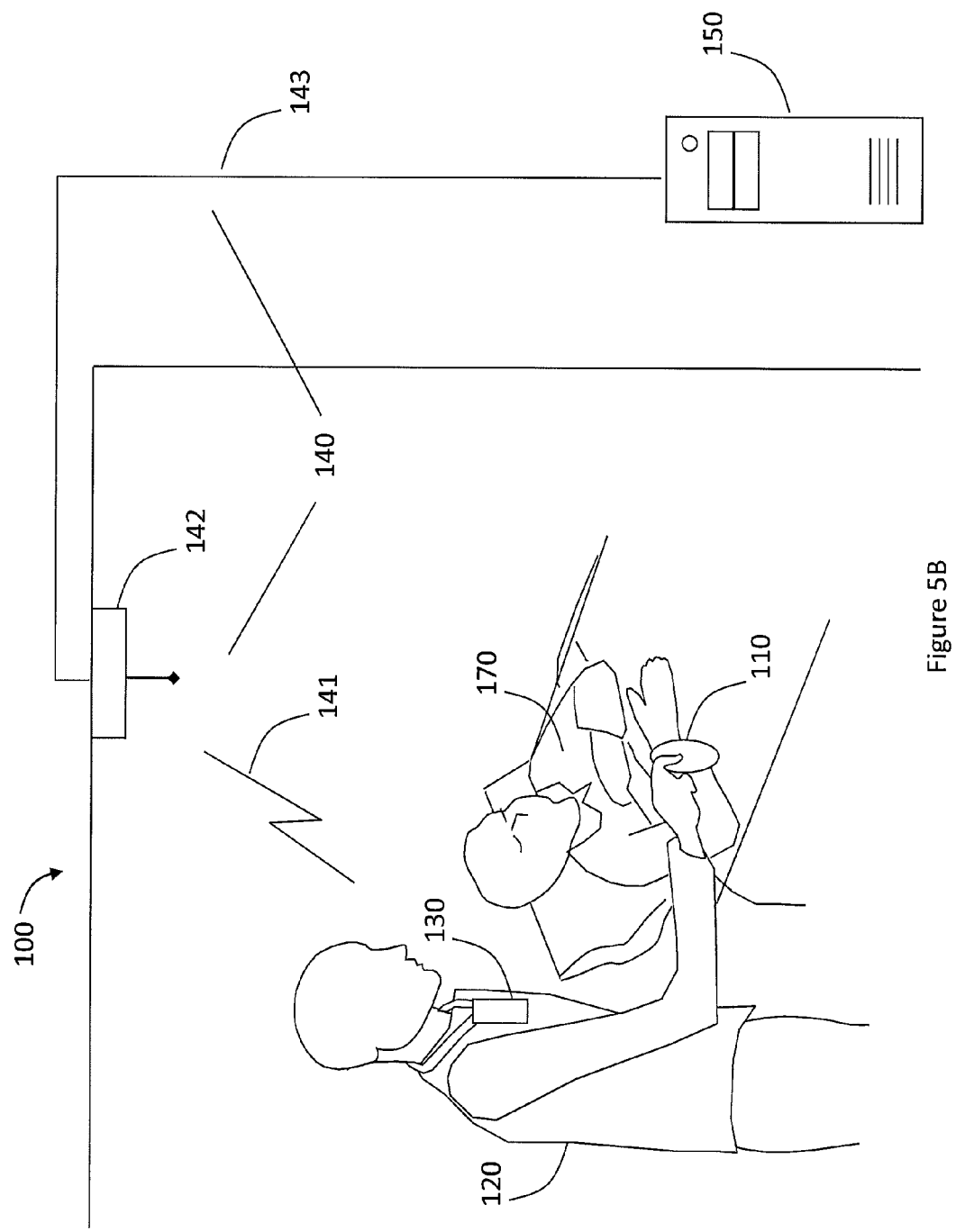
FIG. 5B is an illustrative depiction of another embodiment of the automatic touch identification system of the present invention applied to identifying a patient in a clinical setting.

Another embodiment of an automatic touch identification system 100 applied to positively identifying a patient in a clinical setting is illustrated in FIG. 5B. In this embodiment an identification device 110 is worn on a wristband by a patient (i.e. object 170) which contains identifying information for the patient (i.e. object 170). A clinician (i.e. user 120) is wearing a reading device 130 which is coupled to the clinician (i.e. user 120). According to this embodiment when the clinician (i.e. user 120) touches identifying device 110 the device is also coupled to the clinician (i.e. user 120) and identifying information is conducted or transmitted by or through the clinician (i.e. user 120) to reading device 130. The identifying information may include data about patient (i.e. object 170) obtained from a sensor 115 in identification device 110. In this embodiment reading device 130 is integrated with a wireless communication device which sends the identifying information through network 140 to a server (i.e. computing device 150). According to this embodiment network 140 consists of a WiFi network and a local area network (LAN). Reading device 130 sends the identifying information from identification device 110 and its own identifying information via wireless connection 141 to wireless access point 142. Wireless access point 142 is connected via a LAN 143 to the server (i.e. computing device 150). The server (i.e. computing device 150) receives the identifying information, retrieves related information about the patient (i.e. object 170), verifies that the user 120 is authorized to see patient information, and if verified sends the related information back through the network 140. Reading device 130 receives the related information and displays and/or enunciates the information to the clinician (i.e. user 120).

Figure 6:
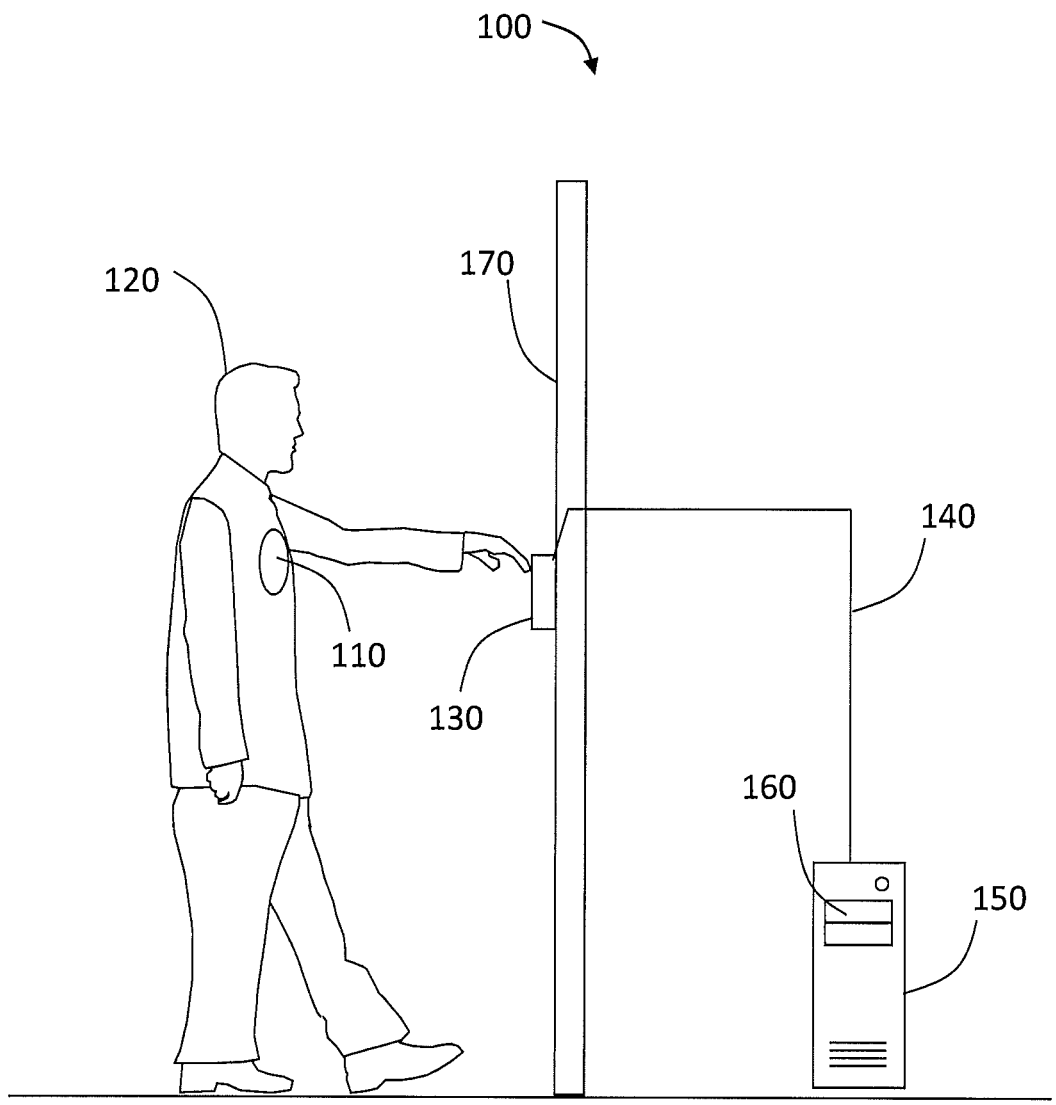
FIG. 6 is an illustrative depiction of the automatic touch identification system of the present invention applied to a door entry system.

FIG. 6 depicts one embodiment of an automatic touch identification system 100 suitable for practicing an illustrative embodiment of the present invention applied to a door entry system (i.e. object 170). In this embodiment an identification device 110 is worn by a user 120 which contains identifying information for the user 120 and is coupled to the user 120. A reading device 130 is integrated with a door entry system (i.e. object 170) which is connected through network 140 to a server (i.e. computing device 150). According to this embodiment when the user 120 touches reading device 130 the reading device 130 is coupled to the user 120 and identifying information is conducted or transmitted by or through the user 120 from identifying device 110 to reading device 130. In this embodiment reading device 130 sends the identifying information from identification device 130 and its own identifying information through network 140 to a server (i.e. computing device 150). According to this embodiment the server (i.e. computing device 150) receives the identifying information, determines if the user 120 is authorized to enter the through the door, and if so sends a signal to the door entry system (i.e. object 170) opening the door. In this embodiment the identifying information, date and time, and action taken are stored in electronic storage 160 which can be later retrieved for reporting or other purposes.

Figure 7:
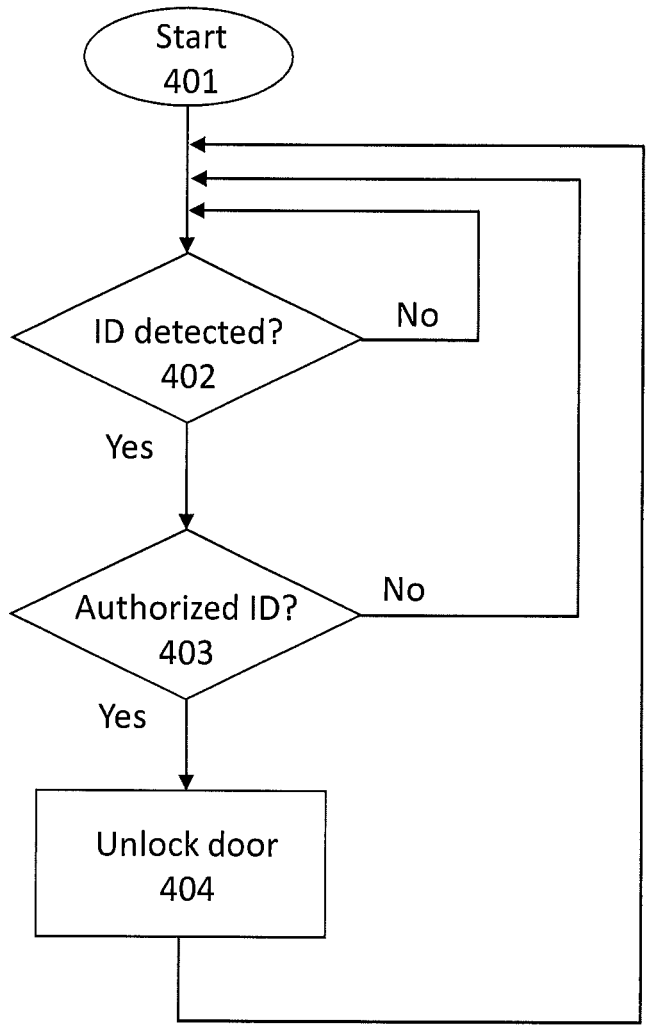
FIG. 7 is a flow diagram of an automatic touch identification system according to the teachings of the present invention applied to a door entry system.

FIG. 7 depicts an embodiment of a process used to manage the door entry system of FIG. 6. Reading device 130 looks for identifying information (an ID) from an identification device 110 which identifies user 120 (step 402). When an ID is received, it is sent to computing device 150 which checks to see if user 120 is authorized to pass through door entry system 170 (step 403). If the user 120 is not authorized to pass through door entry system 170, then the system returns to scan for another ID. If the user 120 is authorized to pass through door entry system 170, then computing device 150 notifies door entry system 170 to unlock the door (step 404) and returns to scan for another ID.

Figure 8:
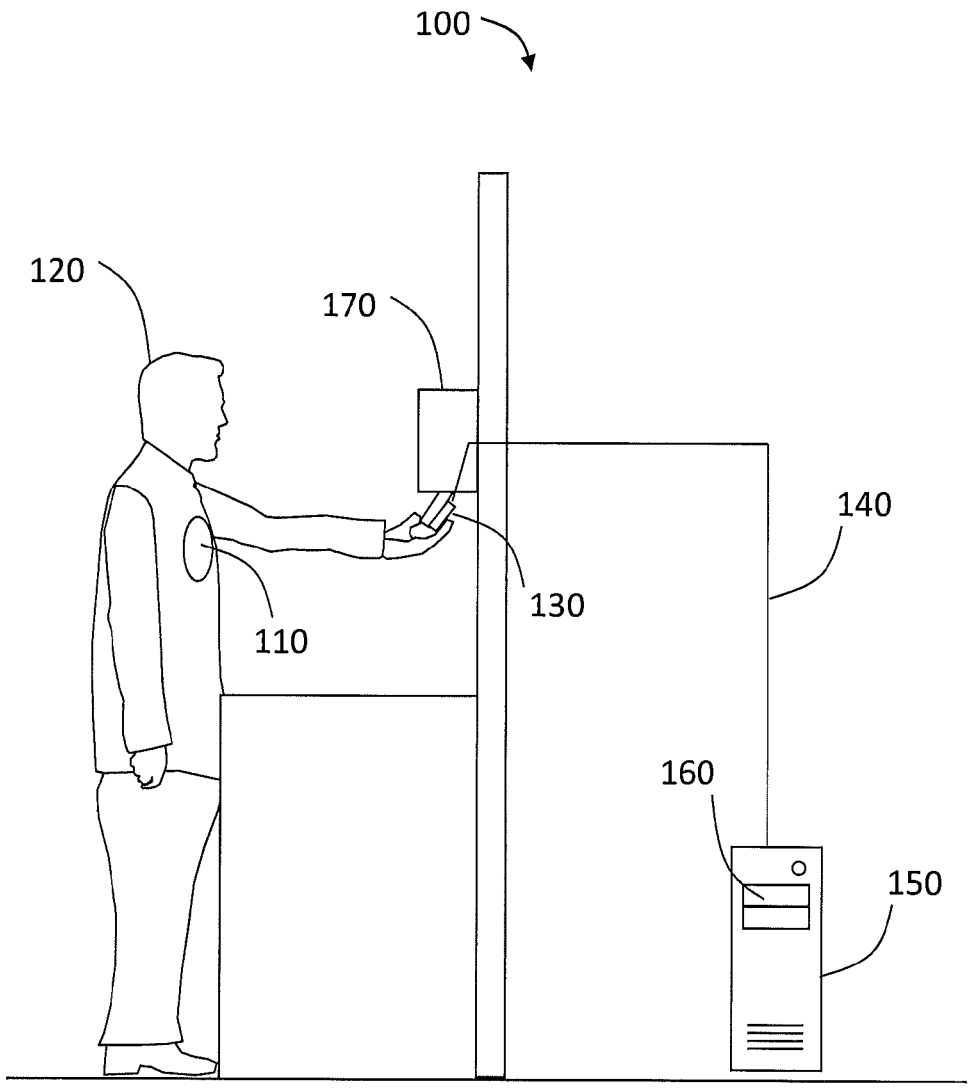
FIG. 8 is an illustrative depiction of the automatic touch identification system of the present invention applied to a hand washing detection system.

FIG. 8 depicts one embodiment of an automatic touch identification system 100 suitable for practicing an illustrative embodiment of the present invention applied to a hand washing detection system. In this embodiment an identification device 110 is worn by a user 120 which contains identifying information for the user 120 and is coupled to the user 120. A reading device 130 is attached to the activating lever of a soap dispenser (i.e. object 170) which is connected through network 140 to a server (i.e. computing device 150). According to this embodiment when the user 120 touches the activating lever reading device 130 is also contacted. This contact results in reading device 130 being coupled to the user 120 and identifying information is conducted or transmitted by or through the user 120 from identifying device 110 to reading device 130. In this embodiment reading device 130 sends the identifying information from identification device 130 and its own identifying information through network 140 to a server (i.e. computing device 150). According to this embodiment the server (i.e. computing device 150) receives the identifying information and determines that the user 120 has used the soap dispenser (i.e. object 170). In this embodiment the identifying information, date and time are stored in electronic storage 160 which can be later retrieved for reporting or other purposes.

Figure 9:
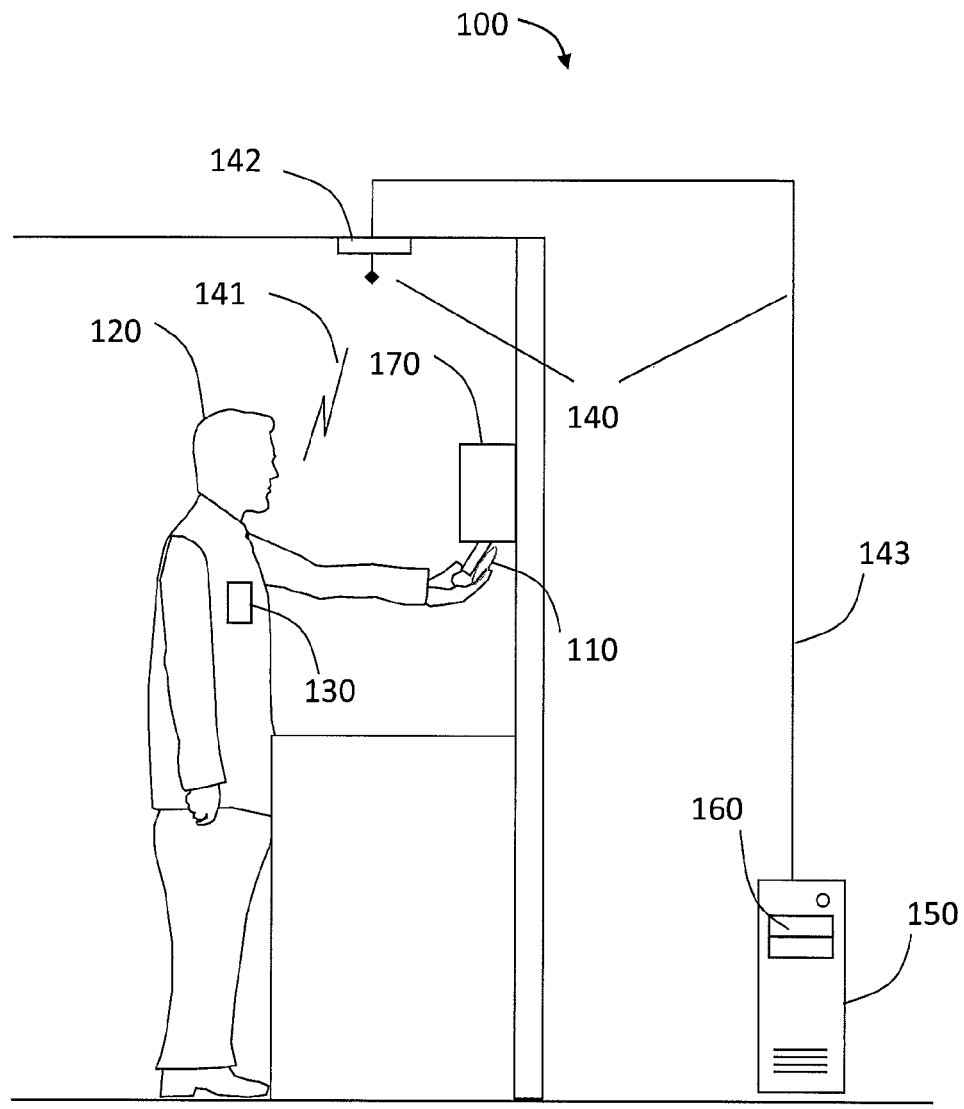
FIG. 9 is an illustrative depiction of the automatic touch identification system of the present invention applied to another implementation of a hand washing detection system.

Another embodiment of an automatic touch identification system 100 applied to a hand washing detection system is illustrated in FIG. 9. In this embodiment a reading device 130 is worn by a user 120 which contains identifying information for the user 120 and is coupled to the user 120. Reading device 130 is also connected through network 140 to a server (i.e. computing device 150). According to this embodiment network 140 consists of a WiFi network and a local area network (LAN). An identification device 110 is attached to the activating lever of a soap dispenser (i.e. object 170). According to this embodiment when the user 120 touches the activating lever, identification device 110 is also contacted. This contact results in identification device 110 being coupled to the user 120 and identifying information is conducted or transmitted by or through the user 120 from identifying device 110 to reading device 130. In this embodiment reading device 130 sends the identifying information from identification device 130 and its own identifying information through network 140 to a server (i.e. computing device 150). According to this embodiment the server (i.e. computing device 150) receives the identifying information and determines that the user 120 has used the soap dispenser (i.e. object 170).

Figure 10:
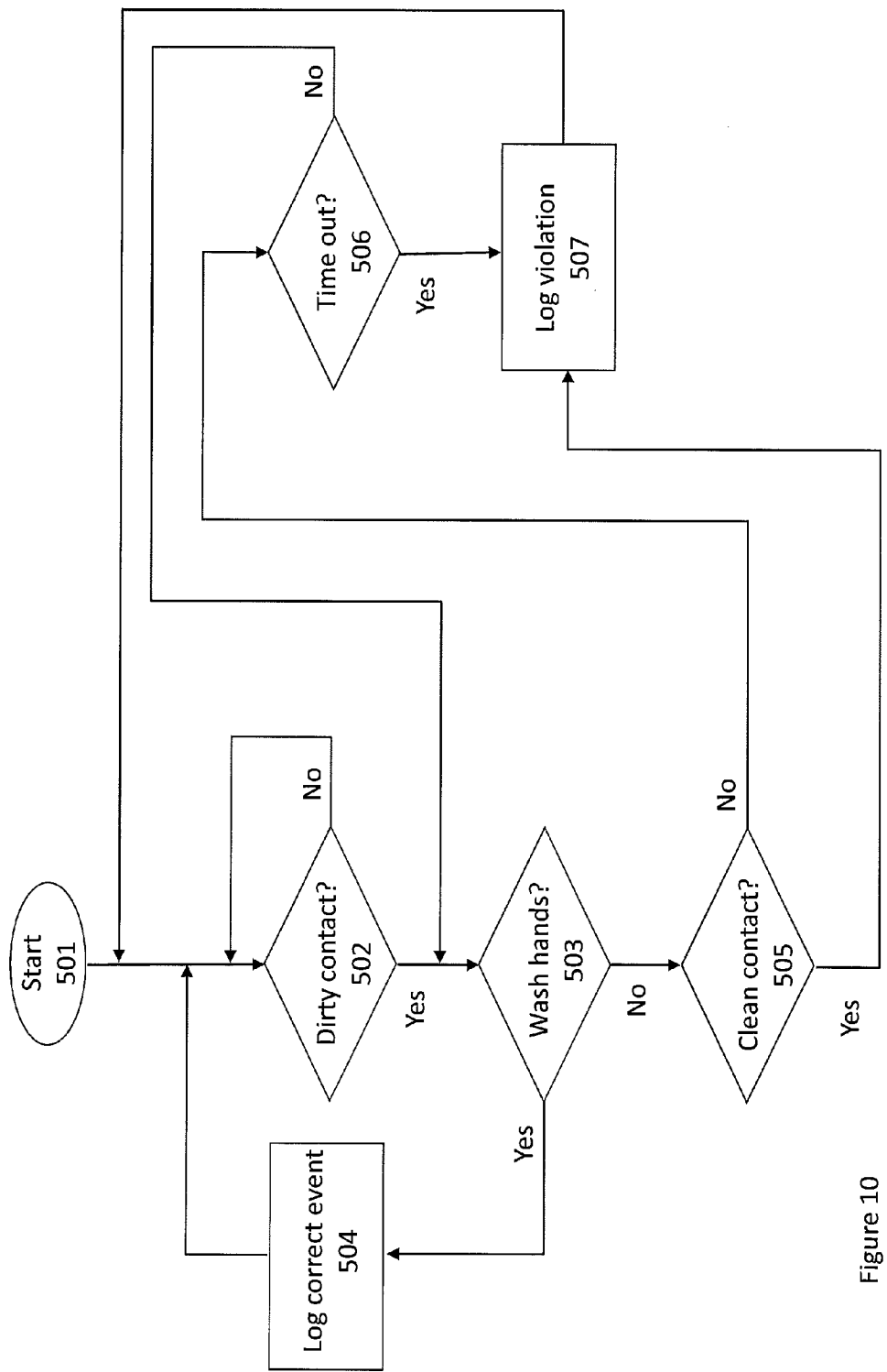
FIG. 10 is a flow diagram of an automatic touch identification system according to the teachings of the present invention applied to a system to monitor hand washing.

FIG. 10 depicts an embodiment of a process used to manage the hand washing system of FIG. 9. The system checks to see if user 120 has come in contact with a dirty object (step 502). Dirty objects can be determined by identifying information from an identification device 110 associated with such objects (e.g. an identification device 110 attached to, or integrated into, a toilet handle). Likewise clean objects can be determined by identifying information from an identification device 110 associated with such objects (e.g. an identification device 110 attached to, or integrated into, a refrigerator handle). After detecting contact with a dirty object, the system checks to see if the user 120 washes his hands (step 503) before touching a clean object (step 505) or before a period of time expires (step 506). If so, the system logs that the user washed his hands appropriately (step 504). If not, then the systems logs that the user was in violation of the hand washing process (step 507).

Figure 11:
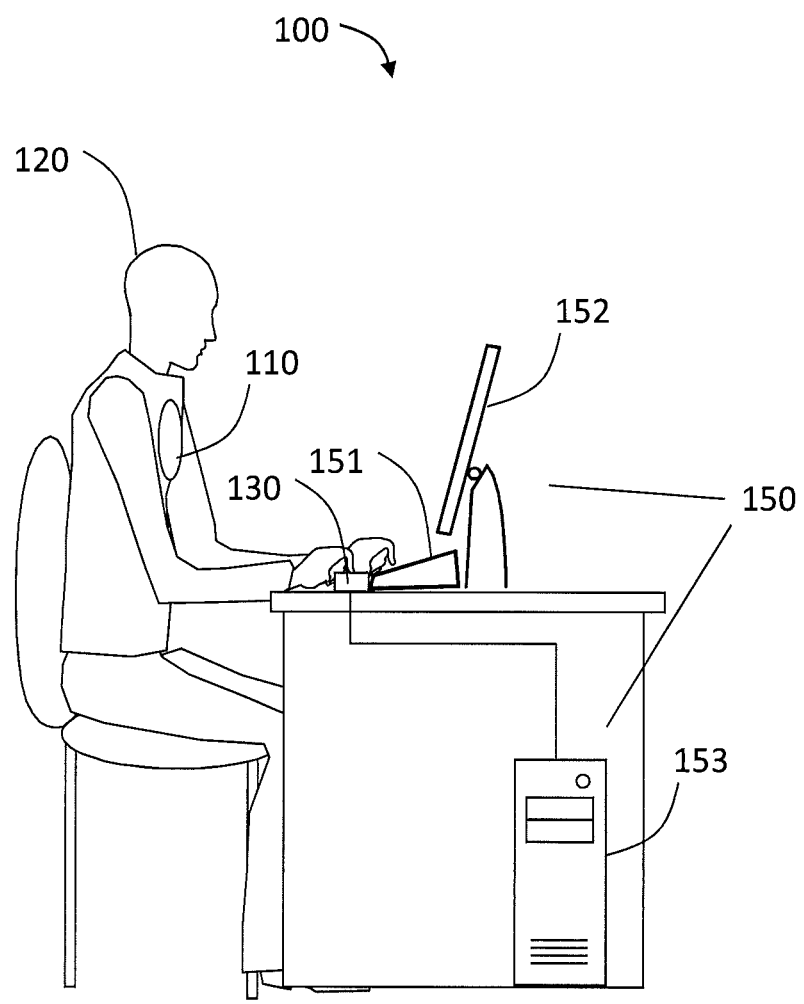
FIG. 11 is an illustrative depiction of the automatic touch identification system of the present invention applied to a computer sign-on/sign-off system.

FIG. 11 depicts one embodiment of an automatic touch identification system 100 suitable for practicing an illustrative embodiment of the present invention applied to a computer sign-on/sign-off system. In this embodiment an identification device 110 is worn by a user 120 which contains identifying information for user 120 and is coupled to the user 120. A reading device 130 is attached or placed near the keyboard 151 which is connected through network 140 to personal computer 153. Keyboard 151, display 152 and personal computer 153 together make up computing device 150 which is also object 170 in this embodiment. According to this embodiment when the user 120 uses keyboard 151 the user 120 also touches or comes in close proximity to reading device 130 which results in reading device 130 being coupled to the user 120 and identifying information is conducted or transmitted by or through the user 120 from identifying device 110 to reading device 130. In this embodiment reading device 130 sends the identifying information from identification device 110 and its own identifying information through network 140 to personal computer 153. According to this embodiment personal computer 153 receives the identifying information from reading device 130 and typing activity from keyboard 151 which it utilizes to manage the sign-on and sign-off of user 120 according to the diagram provided in FIG. 12. Personal computer 153 uses display 152 to convey information and/or instructions to user 120.

Figure 12:
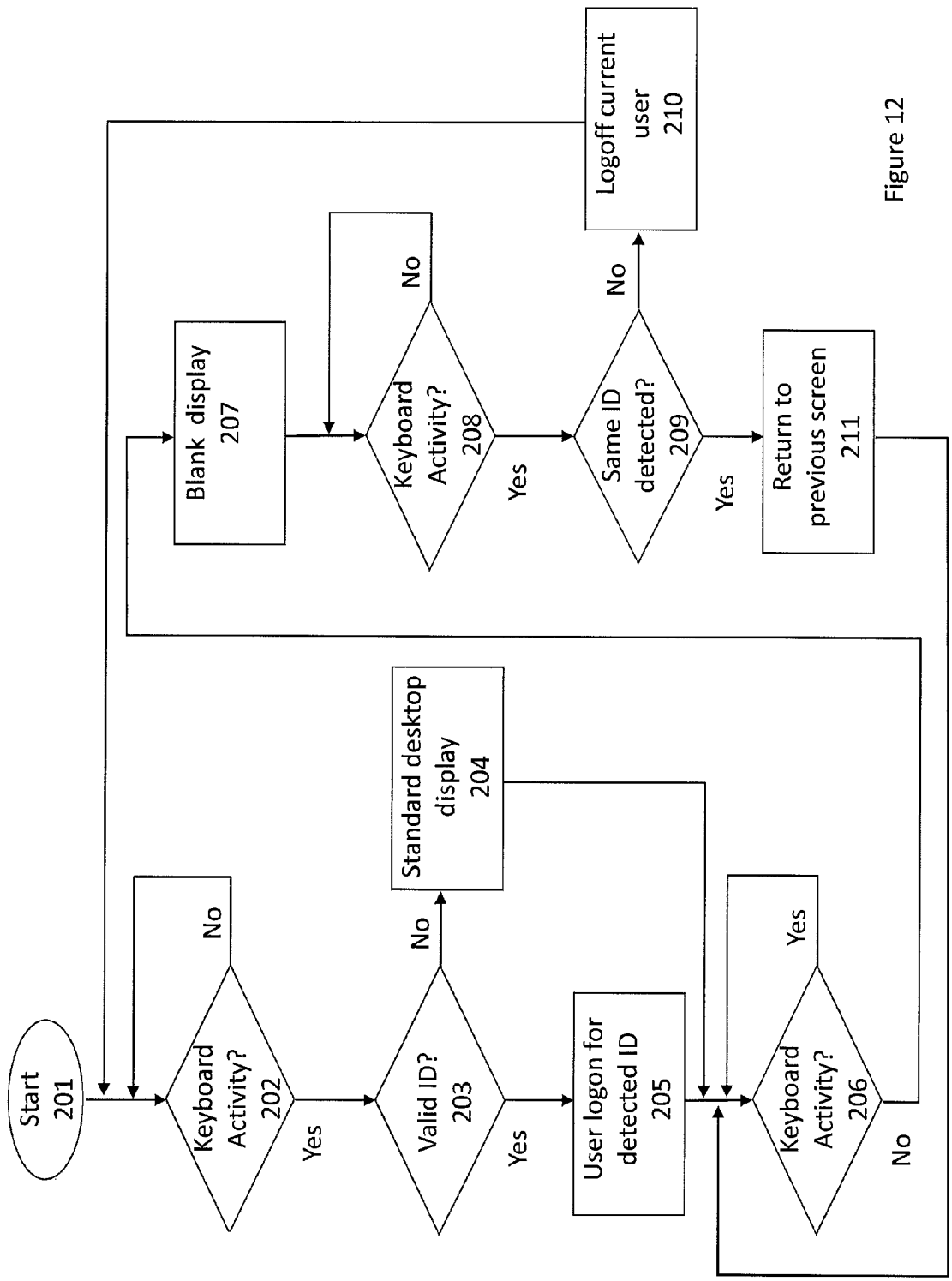
FIG. 12 is a flow diagram of an automatic touch identification system according to the teachings of the present invention applied to a computer sign-on/sign-off system.

FIG. 12 depicts an embodiment of a process used to manage the sign-on/sign-off system of FIG. 11. When keyboard activity is detected (step 202) personal computer 153 checks to see if the identifying information received from reading device 130 contains a valid ID from an identification device 110 (step 203). If a valid ID is present then personal computer 153 displays a logon screen for that user 120 (step 205) on display 152. If a valid ID is not present then a standard desktop display is shown (step 204) on display 152. Once the user 120 has logged onto the system, personal computer 153 monitors the keyboard 151 for activity (step 206). If the keyboard 151 is inactive for a set period of time then personal computer 153 blanks the display 152 (step 207). Blanking the display 152 ensures that sensitive information is not seen by unauthorized people in case keyboard inactivity was due to the user 120 walking away from the system. When keyboard activity is seen again (step 208) personal computer 153 checks to see if the same user 120 is using the keyboard 151, by checking to see if the same identifying information is received from reading device 130 (step 209). If there is no identifying information, the identifying information doesn't match, or the original user did not logon using an identification device 110, then personal computer 153 logs off the original user and returns to start (step 201). If the identifying information matches, then personal computer 153 returns the display 152 to the screen that was present before the display 152 was blanked (step 211) and returns to step 206. If at any time the user 120 logs off then personal computer 153 returns to step 201.

Figure 13:
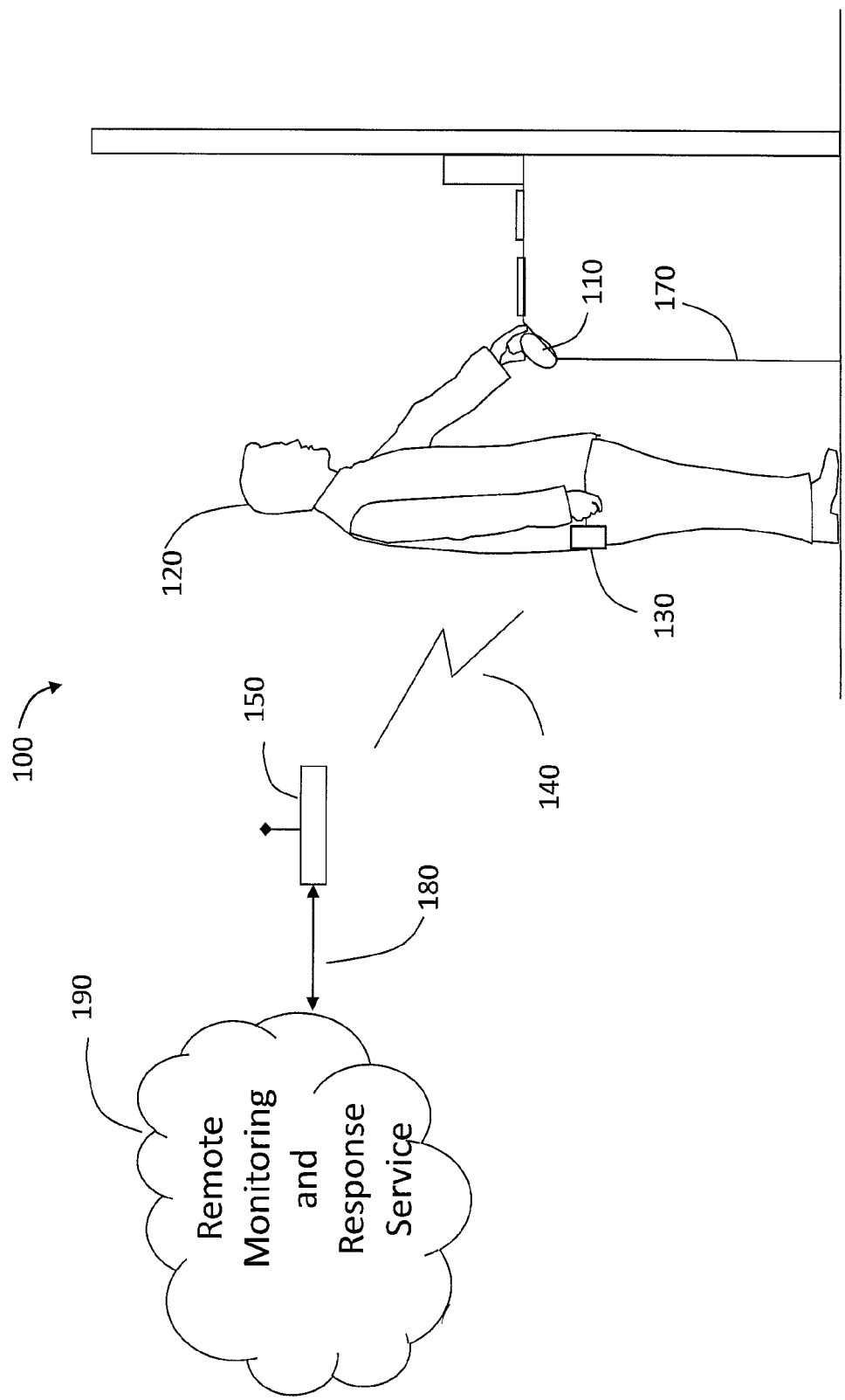
FIG. 13 is an illustrative depiction of the automatic touch identification system of the present invention applied to an activity monitoring system.

FIG. 13 depicts one embodiment of an automatic touch identification system 100 suitable for practicing an illustrative embodiment of the present invention applied to an activity monitoring system. In this embodiment a reading device 130 is worn by a user 120 which contains identifying information for the user 120 and is coupled to the user 120. The reading device 130 is connected through wireless network 140 to a receiver (i.e. computing device 150). The wireless network could be Bluetooth, WiFi, a custom network, or other suitable means. According to this embodiment, identification device 110 is attached to, or integrated into the knob of a stove (i.e. object 170) and contains identifying information for the stove. In this embodiment, when the user 120 touches the stove knob (i.e. identification device 110) the identification device 110 is coupled to the user 120 and identifying information is conducted or transmitted by or through the user 120 from identifying device 110 to reading device 130. Other identification devices may be attached to, or integrated into, other objects providing identifying information for those objects when those identification devices are touched by the user 120. According to this embodiment, reading device 130 sends identifying information received from identification device 110 and its own identifying information through network 140 to the receiver (i.e. computing device 150). In this embodiment the receiver (i.e. computing device 150) receives the identifying information, and forwards it through wide area network 180 to a remote monitoring and response service 190. Remote monitoring and response service 190 and/or the receiver (i.e. computing device 150) utilize the information to provide activity reports, notifications, and alerts based on the activity of user 120. According to this embodiment, notifications and alerts can be sent to reading device 130. This information is communicated to user 120 via the display and enunciating module 133 of reading device 130

Figure 14:
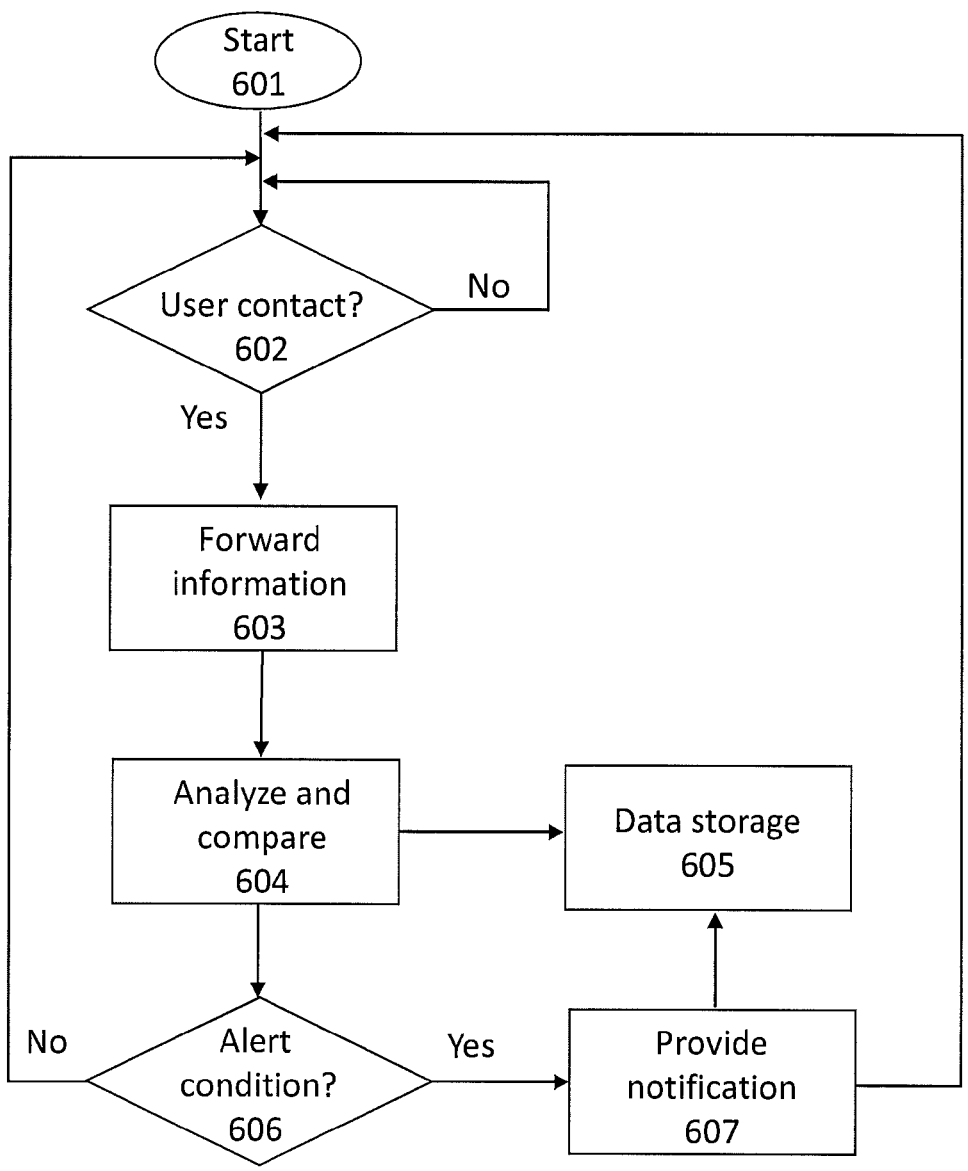
FIG. 14 is a flow diagram of an automatic touch identification system according to the teachings of the present invention applied to an activity monitoring system.

FIG. 14 depicts an embodiment of a process used to manage the activity monitoring system of FIG. 13. The system checks to see if user 120 has come in contact with an identification device 110 (step 602). When contact is made identifying information from identification device 110 is sent to the receiver (i.e. computing device 150), which in turn sends the information to remote monitoring and response service 190 (step 603). The identifying information is analyzed by one or both of the receiver (i.e. computing device 150) and remote monitoring and response service 190 and the data compared to limits for alerting purposes (step 604). The data is compared to alert limits and determination is made if an alert condition has occurred (step 606). If an alert condition has occurred then notification is provided to User 120 through the display and enunciating module 133 of reading device 130 (step 607). Data is retained for future review (step 605).

Figure 15A:
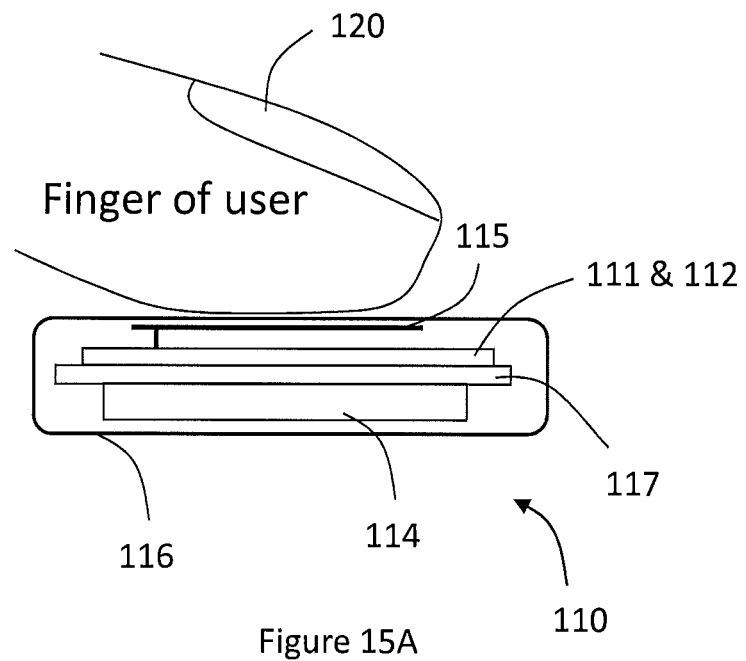
FIG. 15A is an illustrative depiction of an identification device according to the teachings of the present invention.

An example of an identification device 110 according to an embodiment of the current invention is illustrated in FIG. 15A. According to this embodiment, identification device 110 is in the form of a small tag comprised of an enclosure 116 housing a printed circuit board 117 which contains battery 114 on one side and circuitry making up controller 112 and coupling module 111 on the other side. In this embodiment, coupling module 111 includes a conductive coupling plate 115 located on, or just below, the interior surface of enclosure 116. Coupling plate 115 is driven with the identifying signal. When user 120 touches, or comes in very close proximity to, enclosure 116, the body of user 120 is capacitively coupled to identification device 110. Coupling plate 115 can be any conductive element intended to create a capacitive coupling with user 120.

Figure 15B:
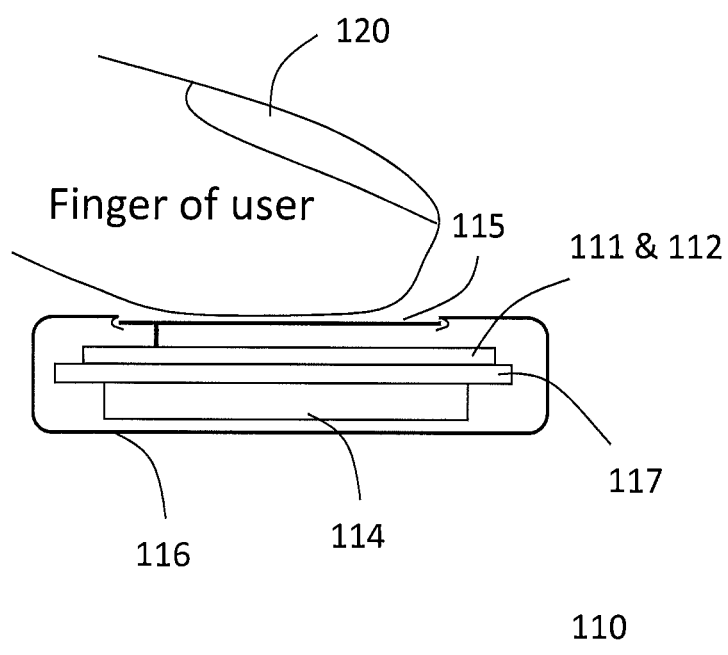
FIG. 15B is an illustrative depiction of another embodiment of an identification device according to the teachings of the present invention.

FIG. 15B illustrates another embodiment of an identification device 110 similar to that shown in FIG. 15A except that coupling plate 115 is exposed. According to this embodiment, identification device 110 is in the form of a small tag comprised of an enclosure 116 housing a printed circuit board 117 which contains battery 114 on one side and circuitry making up controller 112 and coupling module 111 on the other side. In this embodiment, coupling module 111 includes a conductive coupling plate 115 exposed through an opening in enclosure 116. Coupling plate 115 is driven with the identifying signal. When user 120 touches coupling plate 115 with bare skin, the body of user 120 is galvanically connected to identification device 110. When user 120 comes in very close proximity to coupling plate 115, or touches coupling plate 115 through clothing (e.g. glove), the body of user 120 is capacitively coupled to identification device 110. Coupling plate 115 can be any conductive element intended to create a capacitive coupling, a galvanic connection, or a combination of both capacitive coupling and a galvanic connection with user 120.

The same or similar techniques as those illustrated in FIG. 15A and FIG. 15B can be used to couple user 120 to reading device 130 which will be obvious to someone versed in the art.

Figure 16:
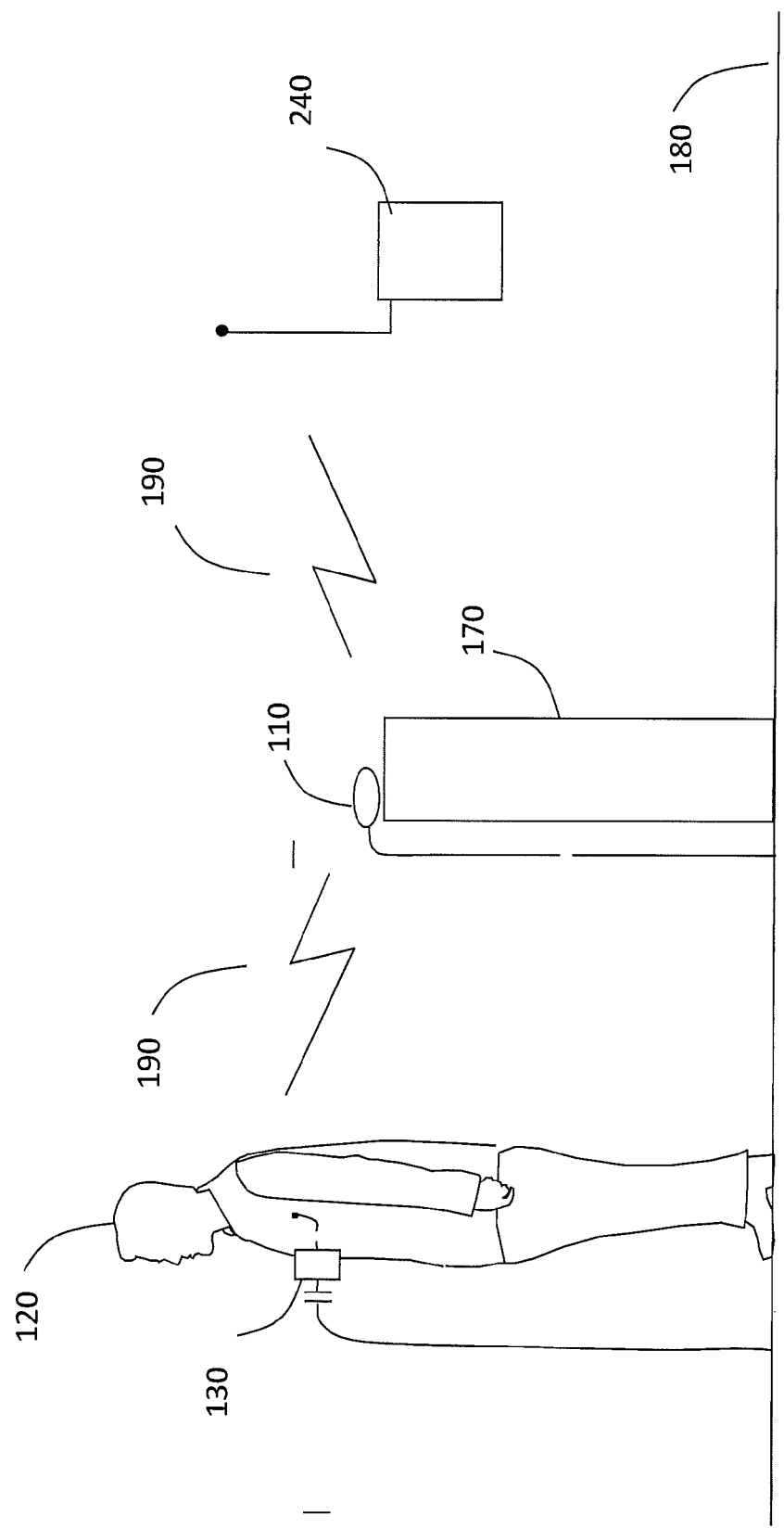
FIG. 16 is an illustrative depiction of the automatic touch identification system of the present invention showing undesirable signal radiation from an identifying device.

According to the embodiment illustrated in FIGS. 15A and 15B, coupling plate 115 and printed circuit board 117 form a "parasitic dipole antenna" that could radiate the identifying signal. As illustrated in FIG. 16, if the modulated carrier from identification device 110 was to radiate from the parasitic dipole antenna, that radiating signal 190 could be picked up by nearby user 120 and conducted or transmitted by or through user 120 to reading device 130, or the radiating signal 190 could be picked up directly by reading device 130, either case resulting in a false indication that user 120 had touched or was in very close proximity to identification device 110. Any such radiating signal 190 could also be picked by a listening device such as a radio receiver 240 which could create a security issue with the system. In addition to the above concerns, it is also desirable to minimize radiation from the parasitic dipole antenna so that identification device 110 can pass radiated emissions regulations and so that it does not need to meet radio regulations for intentional radiators, allowing identification device 110 to be simpler and less expensive than a device designed to meet radio regulations for intentional radiators.

To prevent false indications that user 120 had touched or was in very close proximity to an identification device 110, and to avoid security issues due to the identifying signal being picked by a listening device 240, as well as to meet radiated emissions regulations, the carrier frequency of the identifying signal and the size of the coupling plate 115 must be selected so as to avoid creating a significant radiating signal 190 from the parasitic dipole antenna. Since the efficiency of a dipole antenna is reduced significantly as the size of the dipole becomes a small fraction of the wavelength of the carrier frequency, it is desirable to utilize a carrier frequency and a coupling plate 115 such that the size of the parasitic dipole antenna is a small fraction of the wavelength of the carrier frequency. At the same time, the size of coupling plate 115 must be large enough to allow for adequate coupling between user 120 and identification device 110.

Figure 17A:
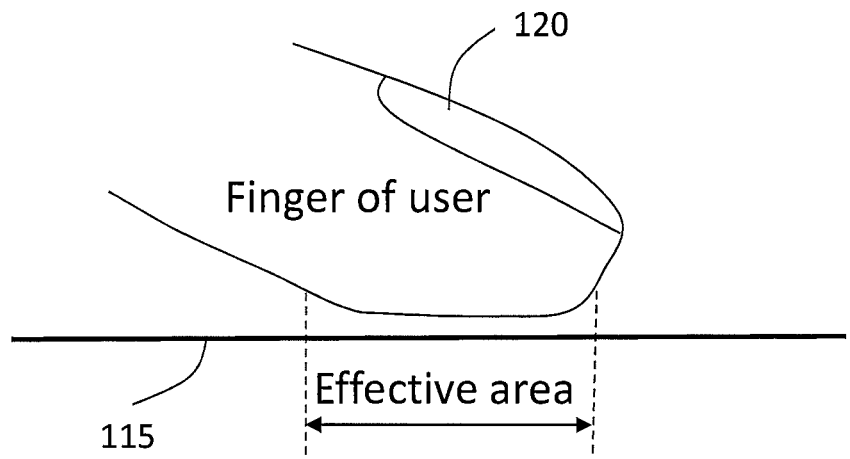
FIG. 17A is an illustrative depiction of the coupling between a user and a coupling plate according to the teachings of the present invention.
Figure 17B:
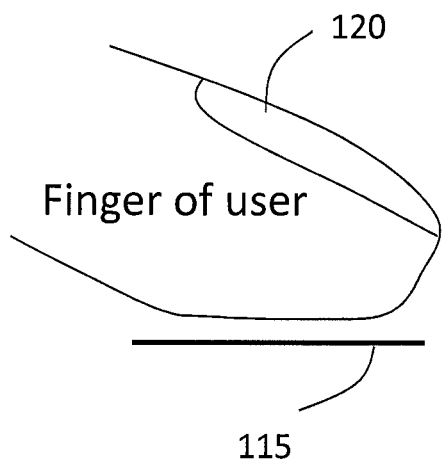
FIG. 17B is an illustrative depiction of another embodiment of the coupling between a user and a coupling plate according to the teachings of the present invention.

Two examples of a coupling plate 115 coupled to the finger of a user 120 according to the current embodiment are shown in FIG. 17A and FIG. 17B. The amount of coupling is proportional to the capacitance between the finger of user 120 and coupling plate 115, which is a function of the area and distance between the finger of user 120 and coupling plate 115. While the coupling plate 115 of FIG. 17A is significantly larger than the coupling plate 115 of FIG. 17B, the amount of capacitance and thus coupling between the finger of user 120 and coupling plate 115 is not increased in proportion to the size of the coupling plate since the distance between the finger of user 120 and coupling plate 115 increases significantly for the area of coupling plate 115 that is not directly under the tip of the finger of user 120 ("effective area"). The effective area of coupling plate 115 of FIG. 17A is approximately the same as the area of coupling plate 115 of FIG. 17B; however, the coupling plate 115 of FIG. 17B has the advantage of radiating less signal at a given carrier frequency than the coupling plate 115 of FIG. 17A.

As stated above, to prevent false indications that user 120 had touched or was in very close proximity to an identification device 110, and to avoid security issues due to the identifying signal being picked up by a listening device 240, as well as to meet radiated emissions regulations, the carrier frequency of the identifying signal and the size of the coupling plate 115 must be selected so as to avoid creating a significant radiating signal 190 from the parasitic dipole antenna. It is desirable to keep the radiating signal to less than 100 µV/m peak at 30 m with an identifying signal of 1 Root Mean Squared Volt ($V_{RMS}$) in amplitude. From the area analysis above, the optimum size of the coupling plate 115 according to the current embodiment is the size of the typical area of a fingertip of a user 120, or about ¾ inch in diameter. A coupling plate 115 of this size results in a parasitic dipole antenna that is approximately 1½ inch in size. To minimize the radiating signal from this parasitic dipole antenna, the carrier frequency needs to be selected such that the radiation efficiency of the parasitic dipole antenna is minimized. These parameters can be calculated based on a comparison to a half-wave dipole antenna.

A half-wave dipole antenna has a radiated power of:

$$V^2/75 \text{ ohms}$$

Where V is the RMS voltage of the applied signal. With an applied signal of 1 $V_{RMS}$ the radiated power is 13.3 mW. At 30 m this equates to 1.176 µW/m² average or 1.75 µW/m² peak. Converting this to V/m the output is 25.6 mV/m at 30 m.

The power ratio of the parasitic dipole antenna compared to a half-wave dipole antenna needs to be:

$$(100 \text{ µV/m})/(25.6 \text{ mV/m})=0.0039$$

Since power is proportional to the square of efficiency, the radiation efficiency of the parasitic dipole must be less than 0.0625 (6.25%).

The radiation efficiency E of a dipole antenna can be approximated by the equation:

$$E=Rr/(Rr+R1)$$

Where Rr is radiation resistance and R1 is the resistance loss of the antenna.

Radiation resistance Rr for a dipole antenna that has a length significantly less than a wavelength of the carrier frequency ("a very small dipole") is determined by:

$$Rr=80*\pi^2(L/W)^2$$

Where L is the length of the very small dipole in meters and W is the wavelength of the carrier frequency in meters. For this analysis R1 is assumed to be:

$$R1=0.001*\text{sqrt}(f/1,000,000)$$

This is based on the use of a copper coupling plate that is approximately 2.5 mm thick, where f is the carrier frequency in Hz.

To minimize the radiating signal 190 from the parasitic dipole antenna of identifying device 110, the radiating efficiency of the parasitic dipole antenna is kept at or below 6.25%. Using a coupling plate 115 of ¾ inch size, the maximum usable carrier frequency is calculated to be 3.02 MHz to keep the radiating efficiency of the parasitic dipole antenna at or below the 6.25% limit. Stated from another perspective, the largest dimension of the coupling plate 115 should be less than about 1/2600 of a wavelength of the carrier frequency.

Figure 18:
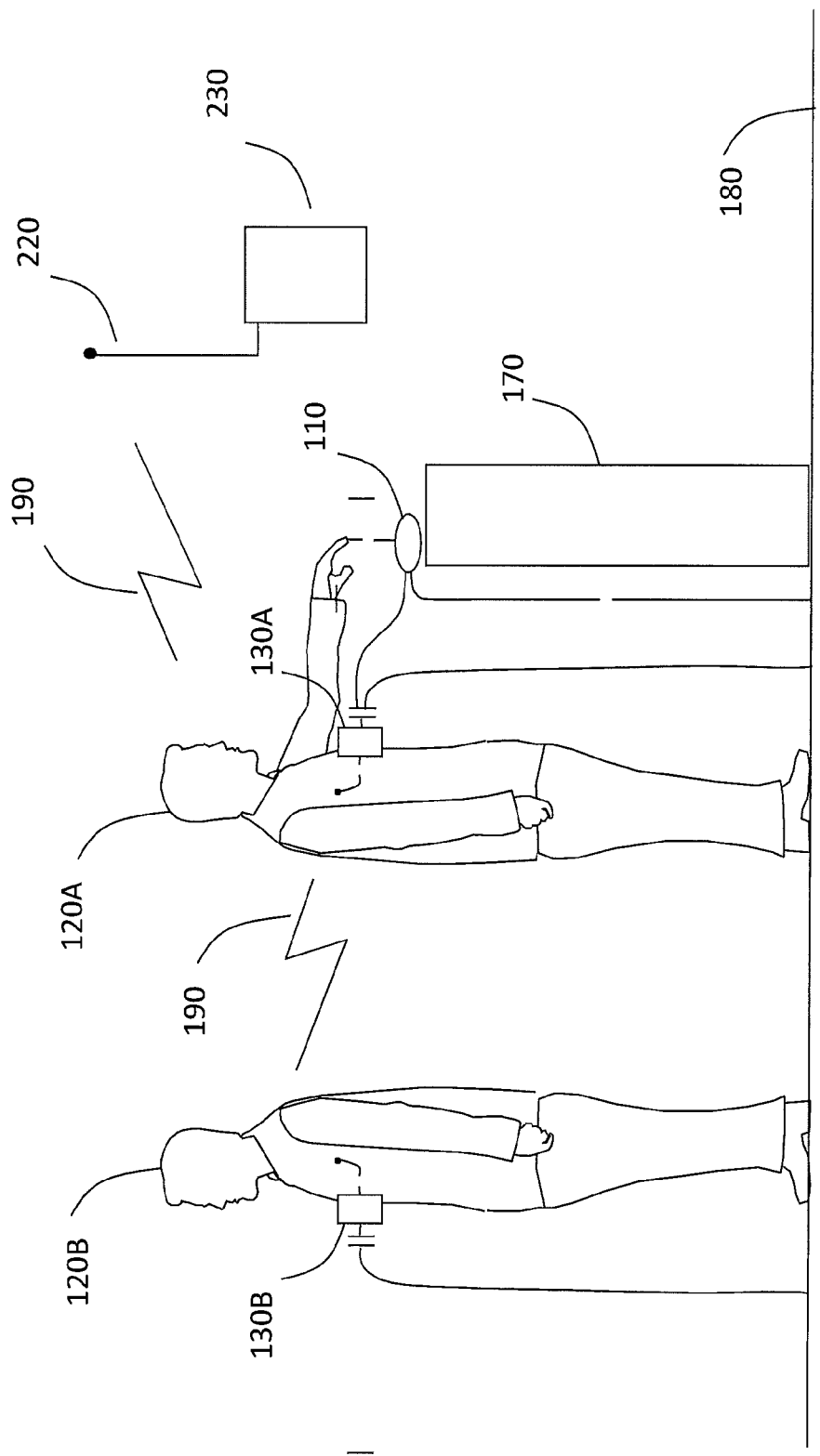
FIG. 18 is an illustrative depiction of the automatic touch identification system of the present invention showing undesirable signal radiation from a user.

There is also a concern about the identifying signal radiating from the body of the user 120. As illustrated in FIG. 18, if the identifying signal from identification device 110 was to radiate from user 120A, that radiating signal 190 could be picked up by nearby user 120B and conducted or transmitted by or through user 120B to reading device 130B, or the radiating signal 190 could be picked up directly by reading device 130B, either case resulting in a false indication that user 120B had touched or was in very close proximity to identification device 110. Any such radiating signal 190 could also be picked by a listening device such as a radio receiver 240 which could create a security issue with the system. In addition to preventing false indications and avoiding security issues, it is desirable to minimize radiation of the identifying signal so that identification device 110 can pass radiated emissions regulations and does not need to meet radio regulations for intentional radiators, allowing identification device 110 to be simpler and less expensive than a device designed to meet radio regulations for intentional radiators.

Figure 19:
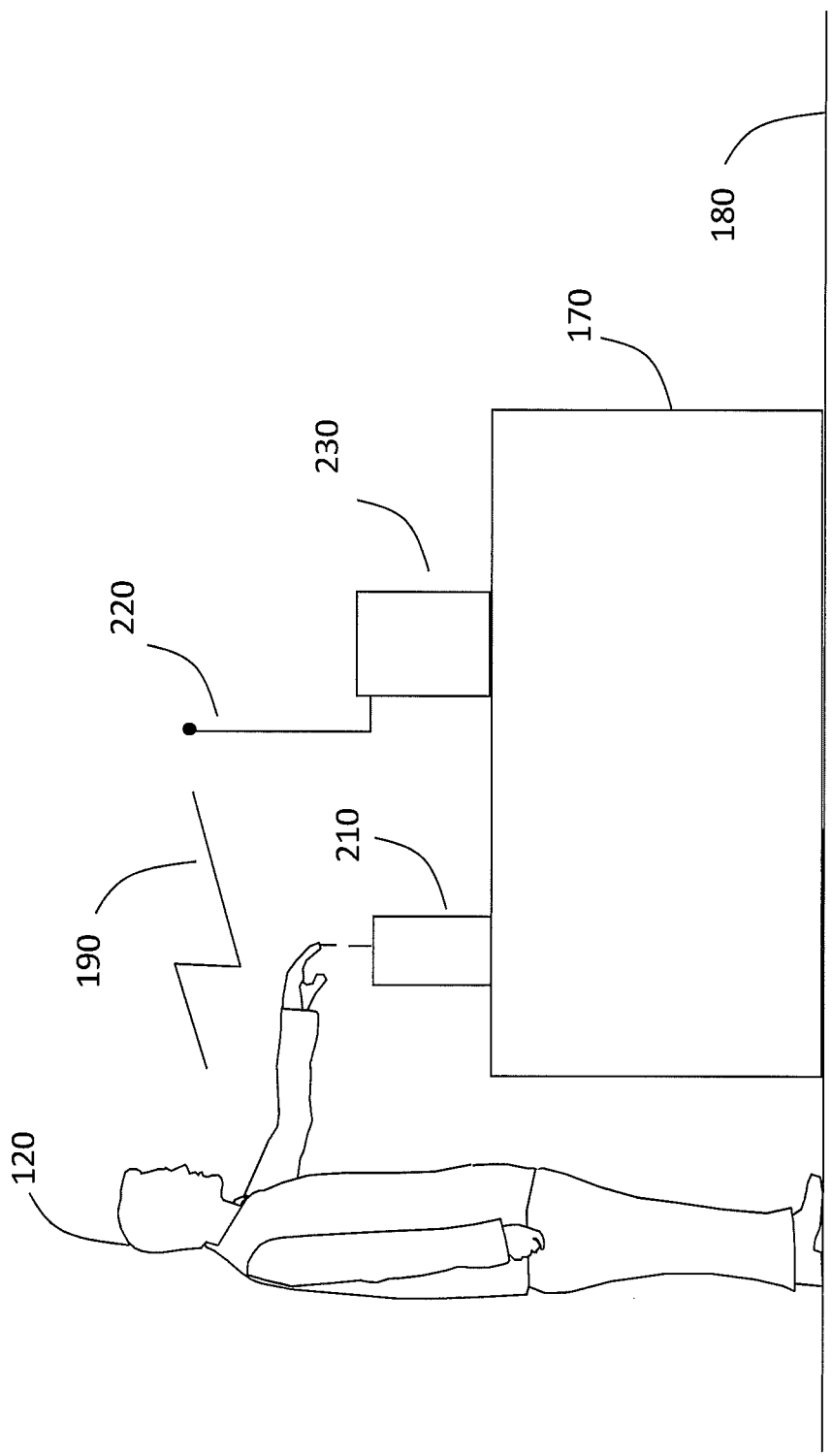
FIG. 19 is an illustrative depiction of a test setup for measuring the signal radiated from the body a user at different operating frequencies.
Figure 21:
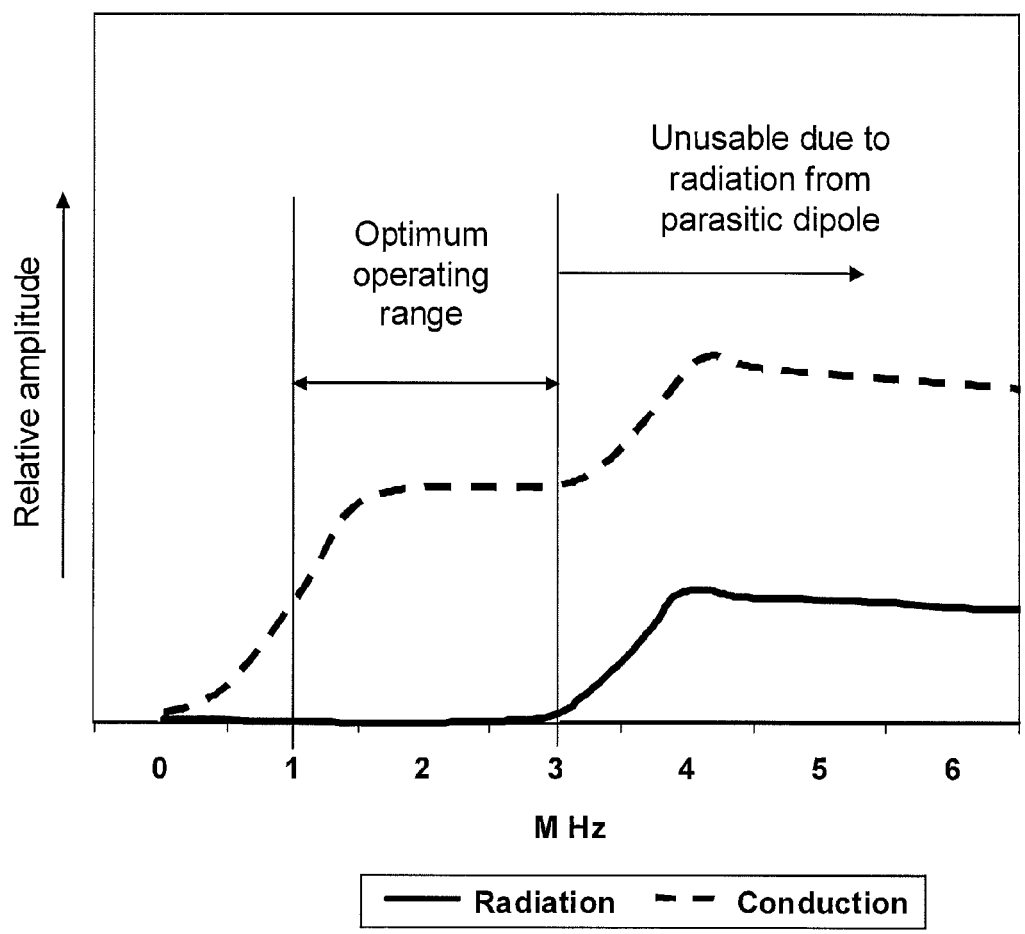
FIG. 21 is a graph illustrating the relative amplitude of signals radiated from the body of a user, and conducted or transmitted by or through a user at different operating frequencies to the teachings of the present invention.

The line labeled "Radiation" in FIG. 21 shows an example of the relative amplitude of the radiated signal from user 120 at various carrier frequencies as determined from the test setup illustrated in FIG. 19. In the test setup of FIG. 19, a test signal is coupled to user 120 from test generator 210 using the coupling method illustrated in FIG. 15A with an upper test limit of 3.02 MHz established above. A test antenna 220 and test receiver 230 are utilized to measure the relative amplitude of the radiating signal 190 from user 120.

Figure 20:
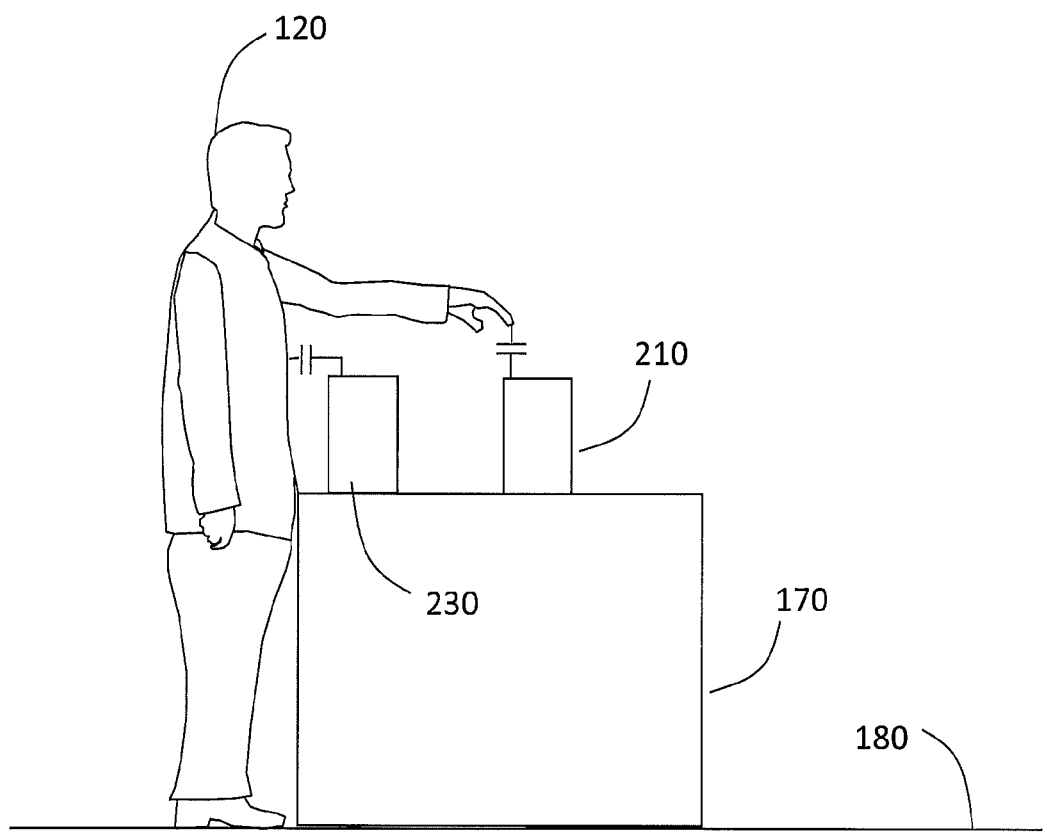
FIG. 20 is an illustrative depiction of a test setup for measuring the signal conducted or transmitted by or through a user at different operating frequencies.

The line labeled "Conduction" in FIG. 21 shows an example of the relative amplitude of the signal conducted or transmitted by or through user 120 at various carrier frequencies as determined from the test setup illustrated in FIG. 20. In the test setup of FIG. 18, a test signal is coupled to user 120 from test generator 210 using the coupling method illustrated in FIG. 15A with an upper test limit of 3.02 MHz established above. A test receiver 230 is also coupled to user 120 in a similar manner and is utilized to measure the relative amplitude of the signal conducted or transmitted by or through user 120.

FIG. 21 shows the example of the relative amplitude of the radiated signal from user 120 ("Radiation" curve) and the relative amplitude of the signal conducted or transmitted by or through user 120 ("Conduction" curve) on the same graph. In this embodiment, the optimum operating range for the carrier frequency is selected to minimize radiation of the identifying signal from the body of user 120, while providing sufficient signal conducted or transmitted by or through user 120 to reliably receive the identifying signal with reading device 130.

In a preferred embodiment of the present invention, coupling module 111 of identification device 110 utilizes a carrier frequency for the identifying signal in the range of about 1 MHz to 3 MHz (about 2 MHz nominal) and coupling module 131 of reading device 130 receives, demodulates, and/or performs other conditioning of the received signal. According to this preferred embodiment, a carrier frequency in the range of about 1 MHz to 3 MHz (about 2 MHz nominal) is utilized to minimize radiation of the identifying signal from the body of user 120, and to have sufficient signal amplitude to reliably receive the identifying signal that is conducted or transmitted by or through user 120 to reading device 130.

Figure 22:
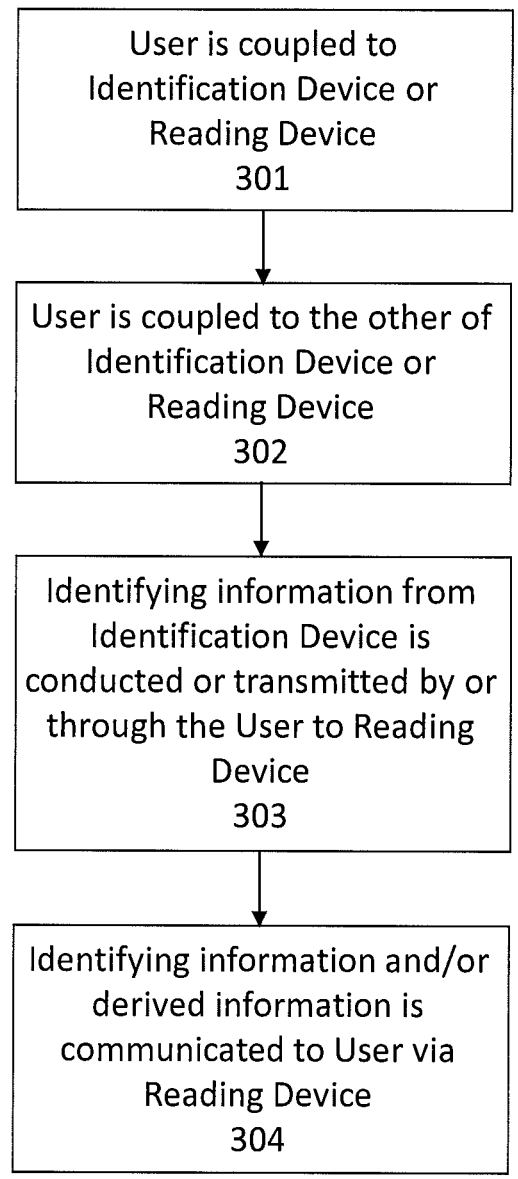
FIG. 22 is a flow diagram describing the coupling of the identification device and the reading device according to an exemplary embodiment of the present invention.

FIG. 22 illustrates a flow diagram describing the coupling of the identification device and the reading device according to an exemplary embodiment of the present invention. As illustrated in step 301, the user is first coupled to an identification device or a reading device. The user may be coupled to the devices by, for example, carrying the device and wearing an item where the device is attached. The user is then coupled to the other of the identification device or the reading device (step 302). The second coupling may be, for example, a galvanic coupling or a capacitive coupling. Once the user is coupled to both the identification device and the reading device, the identifying information from identification device is conducted or transmitted by or through the user to reading device (step 303). The reading device may store identifying information itself and/or may derive information using the identifying information transmitted by the identification device. The identifying information and/or derived information may be communicated to the user via the reading device (step 304). It is possible to match the identifying information on the identification device and the identifying information or the derived information on the reading device using the exemplary method illustrated in FIG. 22.

Figure 23:
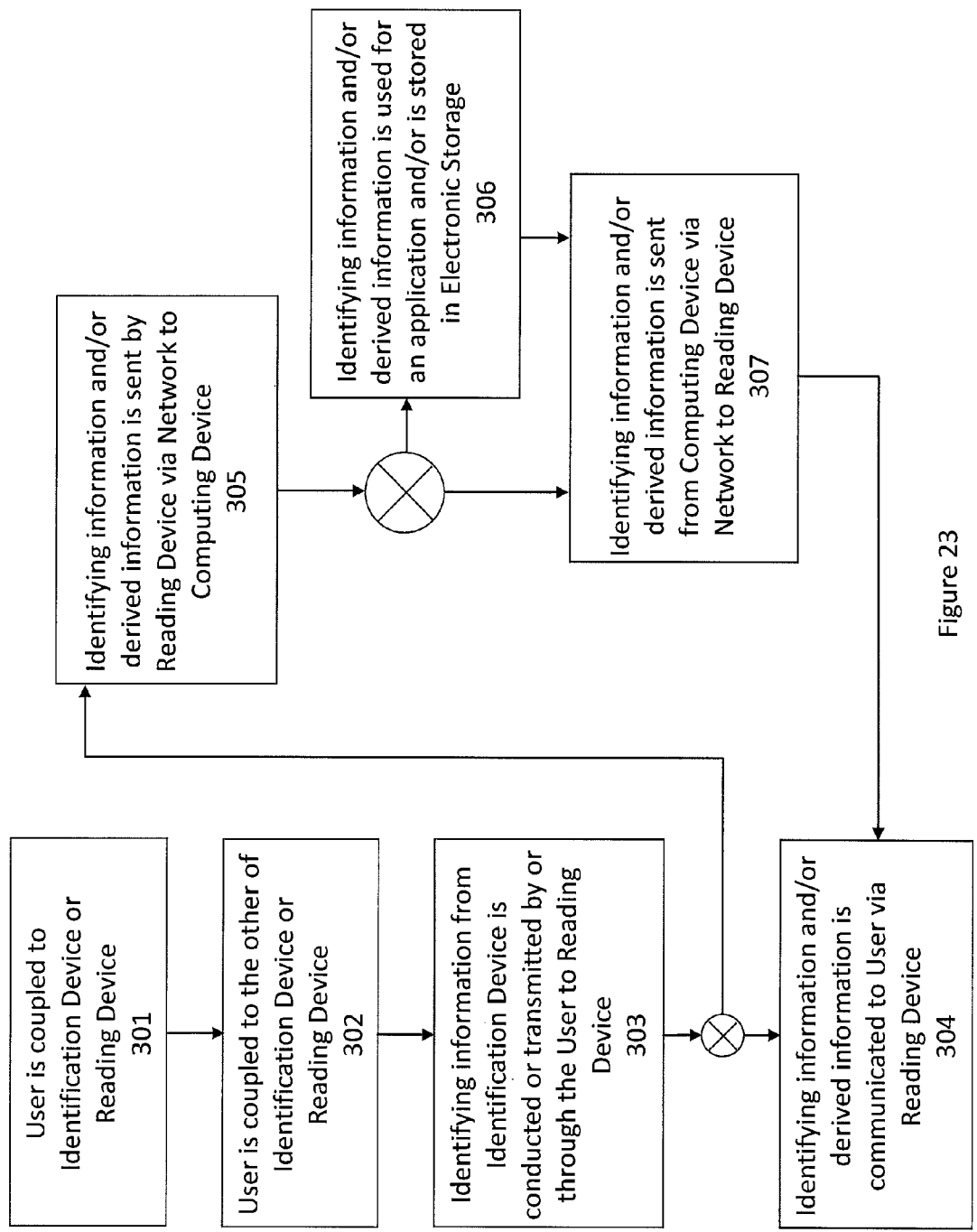
FIG. 23 is a flow diagram describing the coupling of the identification device and the reading device where the reading device communicates with a computing device over a network according to an exemplary embodiment of the present invention.

FIG. 23 illustrates a flow diagram describing the coupling of the identification device and the reading device where the reading device communicates with a computing device over a network according to an exemplary embodiment of the present invention. Similar to the steps described above in connection with FIG. 22, the user is first coupled to an identification device or a reading device (step 301). The user is then coupled to the other of the identification device or the reading device (step 302). Once the user is coupled to both the identification device and the reading device, the identifying information from identification device is conducted or transmitted by or through the user to reading device (step 303). As illustrated in FIG. 23, the reading device may send the identifying information to a computing device via a network connection (step 305). The reading device may derive information from the identifying information received from the identification device. The reading device may send the derived information to the computing device via the network connection. According to various embodiments of the present application, the identifying information may be used for an application and/or stored in an electronic storage connected to the computing device (step 306). The computing device may store identifying information or may derive information from the identifying information sent from the reading device. The computing device may also send the identifying information and/or the derived information to the reading device via the network (step 307). The identifying information and/or derived information may be communicated to the user via the reading device (step 304). It is possible to match the identifying information on the identification device and the identifying information or the derived information on the reading device using the exemplary method illustrated in FIG. 23.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

I claim:

1. An identification system for transmitting or receiving information via a user, comprising:
   an identification device for transmitting identifying information via the user, wherein the identification device includes a first coupling module configured to couple the identification device to the user, and a reading device for receiving the identifying information from the identification device via the user, wherein the reading device includes a second coupling module configured to couple the reading device to the user, wherein the first coupling module of the identification device transmits the identifying information to the reading device via the user over a carrier frequency having a frequency between about 1 MHz and about 3 MHz.

2. The identification system of claim 1, wherein
the first coupling module is configured to couple the identification device to the user by a capacitive type coupling, and
the second coupling module is configured to couple the reading device to the user by a capacitive type coupling.

3. The identification system of claim 1, wherein
the first coupling module is configured to couple the identification device to the user by a galvanic type coupling, and
the second coupling module is configured to couple the reading device to the user by a galvanic type coupling.

4. The identification system of claim 1, wherein
the first coupling module is configured to couple the identification device to the user by a capacitive type coupling, and
the second coupling module is configured to couple the reading device to the user by a galvanic type coupling.

5. The identification system of claim 1, wherein
the first coupling module is configured to couple the identification device to the user by a galvanic type coupling, and
the second coupling module is configured to couple the reading device to the user by a capacitive type coupling.

6. An identification device for transmitting identifying information via a user, comprising a coupling module configured to
couple the identification device to the user,
couple the identification device to surrounding environment, and
transmit identifying information via the user using a carrier frequency having a frequency between about 1 MHz and about 3 MHz.

7. The identification device of claim 6, wherein the coupling module is configured to
couple the identification device to the user by a capacitive type coupling, and
couple the identification device to a surrounding environment by a capacitive type coupling.

8. The identification device of claim 6, wherein the coupling module is configured to
couple the identification device to the user by a galvanic type coupling, and
couple the identification device to a surrounding environment by a galvanic type coupling.

9. The identification device of claim 6, wherein the coupling module is configured to
couple the identification device to the user by a capacitive type coupling, and
couple the identification device to a surrounding environment by a galvanic type coupling.

10. The identification device of claim 6, wherein the coupling module is configured to
couple the identification device to the user by a galvanic type coupling, and
couple the identification device to a surrounding environment by a capacitive type coupling.

11. An identification device for transmitting identifying information via a user, using a carrier frequency, comprising:
a coupling module configured to
couple the identification device to the user by a capacitive type coupling or a galvanic type coupling, wherein a coupling plate is employed and has a largest dimension equal to or less than about $1/2600$ of a wavelength of the carrier frequency,
couple the identification device to a surrounding environment by a capacitive type coupling or a galvanic type coupling, and
transmit identifying information via the user using a carrier,
wherein communication by the identification device is based on a capacitive type coupling or a galvanic type coupling to the user without relying upon radiation of a communication signal.

12. A reading device for receiving identifying information via a user, comprising:
a coupling module configured to
couple the reading device to the user,
couple to a surrounding environment, and
receive identifying information via the user at a carrier frequency having a frequency between about 1 and about 3 MHz.

13. The reading device of claim 12, wherein the coupling module is configured to
couple the identification device to the user by a capacitive type coupling, and
couple the identification device to a surrounding environment by a capacitive type coupling.

14. The reading device of claim 12, wherein the coupling module is configured to
couple the identification device to the user by a galvanic type coupling, and
couple the identification device to a surrounding environment by a galvanic type coupling.

15. The reading device of claim 12, wherein the coupling module is configured to
couple the identification device to the user by a capacitive type coupling, and
couple the identification device to a surrounding environment by a galvanic type coupling.

16. The reading device of claim 12, wherein the coupling module is configured to
couple the identification device to the user by a galvanic type coupling, and
couple the identification device to a surrounding environment by a capacitive type coupling.

17. A method of verifying identifying information from an identification device, the method comprising:
coupling an identification device to a user via one or more of a capacitive coupling and a galvanic coupling using a first coupling module;
coupling a reading device to the user via one or more of a capacitive coupling and a galvanic coupling using a second coupling module;
transmitting, by the first coupling module, identifying information from the identification device to the reading device via the user over a carrier having a frequency between about 1 Mhz and about 3 MHz; and receiving, at the reading device, the identifying information transmitted by the identification device via the user.

18. An identification bracelet, comprising:

an identification device for transmitting identifying information via a user, wherein the identification device includes a first coupling module configured to couple the identification device to the user, wherein the first coupling module of the identification device transmits the identifying information to a reading device via the user over a carrier frequency having a frequency less than or equal to about 3 MHz.

19. The identification bracelet of claim 18, wherein the carrier frequency is between about 1 MHz and about 3 MHz.

* * * * *